(12) United States Patent
Shibanuma et al.

(10) Patent No.: US 6,972,334 B1
(45) Date of Patent: Dec. 6, 2005

(54) BATHOPHENATHROLINE COMPOUND AND PROCESS FOR PREPARING SAME

(75) Inventors: Tetsuo Shibanuma, Kanagawa (JP); Yasunori Kijima, Tokyo (JP); Nobutoshi Asai, Kanagawa (JP); Shinichiro Tamura, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 09/704,968

(22) Filed: Nov. 2, 2000

(30) Foreign Application Priority Data

Nov. 2, 1999 (JP) ............................... P11-312071

(51) Int. Cl.[7] ........................................... C07D 471/04
(52) U.S. Cl. .............. 546/88; 252/301.16; 252/301.26; 534/551; 534/560
(58) Field of Search ..................... 546/88; 252/301.16, 252/301.26; 534/551, 560

(56) References Cited

U.S. PATENT DOCUMENTS 3,951,833 A * 4/1976 Juda ........................ 252/51.5 R
4,853,090 A * 8/1989 Daniel et al. ............. 205/781.5
5,262,526 A * 11/1993 Sasamoto .................... 534/551

FOREIGN PATENT DOCUMENTS

EP         0564224      10/1993
WO         WO99/53724   10/1999

OTHER PUBLICATIONS

Sugihara H et al. Anal. Sci. (1993), 9(5), 593-7.*
Dietrich-Buchecker CO et al. Tetrahedron Lett. (1986), 27(20), 2257-60.*
Sugihara, H. et al.; Lithium Ion-Selective Electrodes Based on 1,10-Phenanthroline Derivatives, *Analytical Sciences*, Oct. 1993, vol. 9, pp. 593-597.
Case, F. et al. Substituted 1,10-Phenanthrolines, VIII. 2- and 3-Phenyl Derivatives, *Journal of Organic chemistry*, Oct. 1955, vol. 20, pp. 1330-1336.
Dietrich-Buchecker, C. O., Direct Synthesis of Disubstituted Aromatic Polyimine Chelates, *Tetrahedron Letters.*, 1982, vol. 23, No. 50, pp. 5291-5294.
Dietrich-Buchecker, C. O., Interlocked Macrocyclic Ligands: A Catenand Whose Rotation of One Ring Into The Other Is Precluded By Bulky Substituents, *Tetrahedron Letters*, 1986, vol. 27, No. 20, pp. 2257-2260.

* cited by examiner

*Primary Examiner*—Evelyn Mei Huang
(74) *Attorney, Agent, or Firm*—Sonnenschein, Nath & Rosenthal LLP

(57) ABSTRACT

A novel bathophenanthroline compound of the general formula [I] or [II] is provided General Formula [I]:

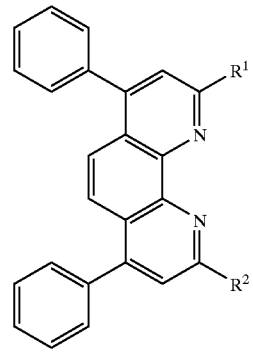

General Formula [II]:

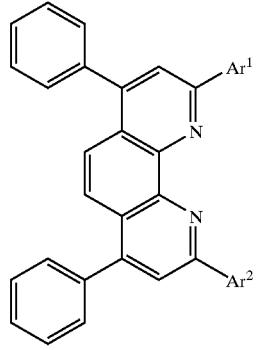

wherein $R^1$ and $R^2$ may be the same or different and independently represent a linear, branched or cyclic, saturated or unsaturated hydrocarbon group, or a substituted or unsubstituted, saturated or unsaturated hydrocarbon group provided that at least one of $R^1$ and $R^2$ has at least two carbon atoms, and wherein $Ar^1$ and $Ar^2$ may be the same or different and independently represent a substituted or unsubstituted aryl group. A process for preparing the compound is also provided wherein bathophenanthroline and an organolithium compound are subjected to nucleophilic substitution reaction to obtain the compound of the above formula [I] or [II].

1 Claim, 7 Drawing Sheets

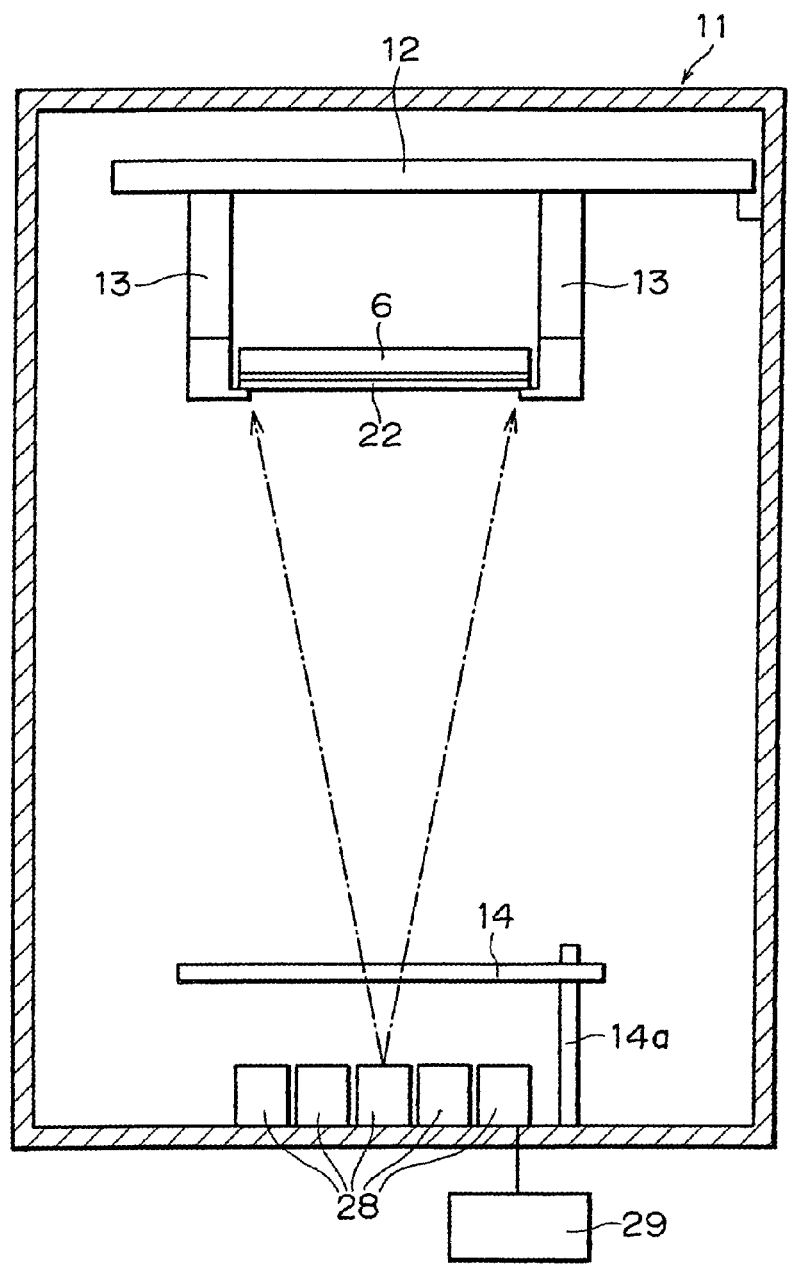
F I G. 3

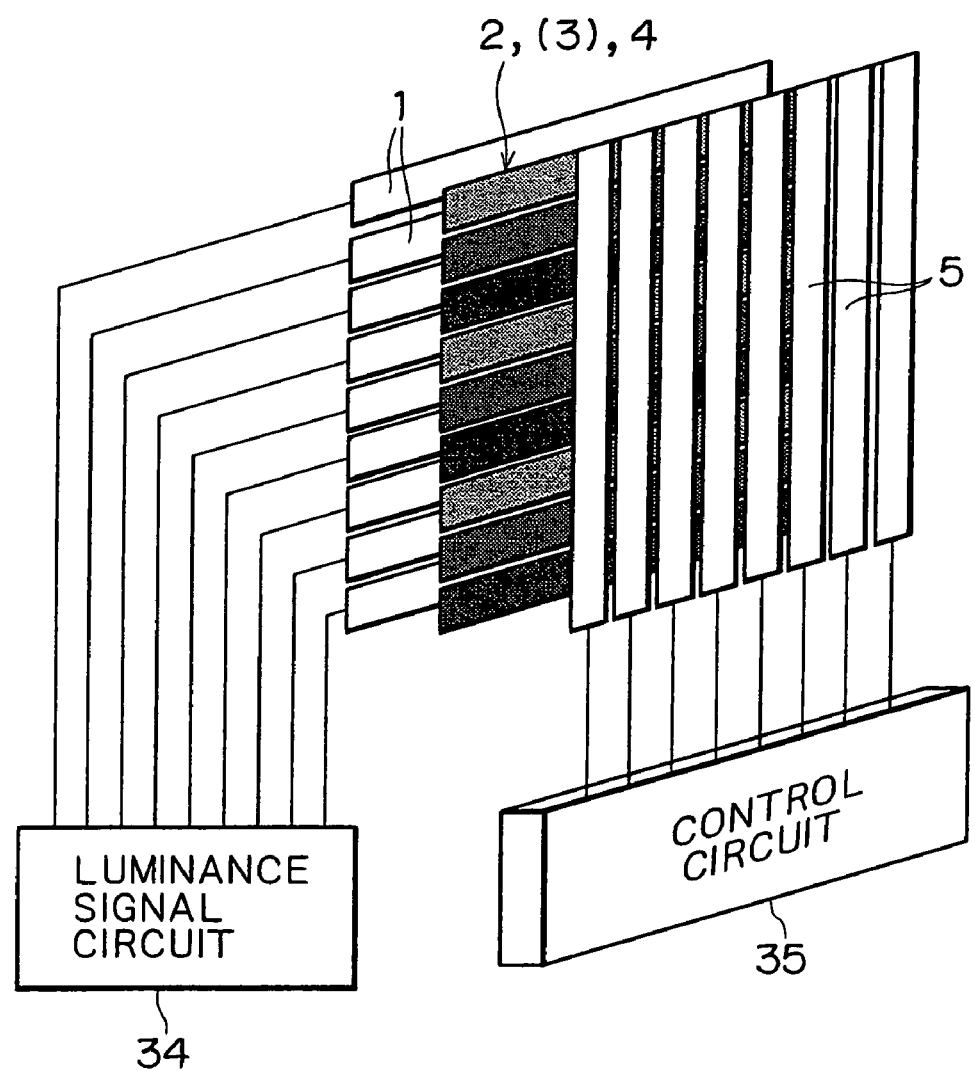

BATHOPHENATHROLINE COMPOUND AND PROCESS FOR PREPARING SAME

RELATED APPLICATION DATA

The present application claims priority to Japanese Application No. P11-312071 filed Nov. 2, 1999, which application is incorporated herein by reference to the extent permitted by law.

BACKGROUND OF THE INVENTION

This invention relates to a bathophenanthroline compound, which is adapted for use in an organic electroluminescent device (e.g. an organic electroluminescent device suitable as a display device or a light-emitting device such as a spontaneous light flat display, especially an organic electroluminescent color display using an organic thin film as an electroluminescent layer), and also a process for preparing the compound.

In recent years, importance of interfaces between human beings and machines including multimedia-oriented commercial articles is exalted. For more comfortable and more efficient machine operations, it is necessary to retrieve information from an operated machine without failure simply, instantaneously and in an adequate amount. To this end, studies have been made on various types of display devices or displays.

As machines are now miniaturized, there is an increasing demand, day by day, for miniaturization and thinning of display devices. For instance, there is an inconceivable development with respect to the miniaturization of lap top-type information processors of the all-in-one type such as notebook-size personal computers, notebook-size word processors and the like. This, in turn, entails a remarkable technical innovation on liquid crystal displays for use as a display device for the processor.

Nowadays, liquid crystal displays are employed as an interface of a diversity of articles and have wide utility in the fields not only of lap top-type information processors, but also of articles for our daily use including small-sized television sets, watches, desk-top calculators and the like.

These liquid crystal displays have been studied as a key of display devices, which are used as the interface connecting a human being and a machine and cover small-sized to large capacitance display devices while making use of the feature that liquid crystals are low in drive voltage and power consumption. However, liquid crystal displays have the problems that they do not rely on spontaneous light and thus need a greater power consumption for back light drive than for liquid crystal drive, with the result that a service time is shortened when using a built-in battery, thus placing a limitation on their use. Moreover, the liquid crystal display has another problem that it has such a narrow angle of field as not to be suitable for use as a large-sized display device.

Furthermore, the liquid crystal display depends on the manner of display using the orientation of liquid crystal molecules, and this is considered to bring about a serious problem that its contrast changes depending on the angle even within an angle of field.

From the standpoint of drive systems, an active matrix system, which is one of drive systems, has a response speed sufficient to deal with a motion picture. However, since a TFT (thin film transistor) drive circuit is used, a difficulty is involved in making a large screen size owing to the pixel defects, thus being disadvantageous in view of the reduction in cost.

In the liquid crystal display, a simple matrix system, which is another type of drive system, is not only low in cost, but also relatively easy in making a large screen size. However, this system has the problem that its response speed is not enough to deal with a motion picture.

In contrast, a spontaneous light display device is now under study such as on a plasma display device, an inorganic electroluminescent device, an organic electroluminescent device and the like.

The plasma display device employs plasma emission in a low pressure gas for display and is suited for the purposes of a large size and large capacitance, but has the problem on thinning and costs. In addition, an AC bias of high potential is required for its drive, and thus, the display is not suitable as a portable device.

The inorganic electroluminescent device has been put on the market as a green light emission display. Like the plasma display device, an AC bias drive is essential, for which several hundreds of volts are necessary, thus not being of practical use.

In this connection, however, emission of three primaries including red (R), green (G) and blue (B) necessary for color display has been succeeded due to the technical development. Since inorganic materials are used for this purpose, it has been difficult to control emission wavelengths depending on the molecular design or the like. Thus, it is believed that full color display is difficult.

On the other hand, the electroluminescent phenomenon caused by organic compounds has been long studied ever since there was discovered a luminescent or emission phenomenon wherein carriers are injected into the single crystal of anthracene capable of emitting a strong fluorescence in the first part of 1960s. However, such fluorescence is low in brightness and monochronous in nature, and the single crystal is used, so that this emission has been made as a fundamental investigation of carrier injection into organic materials.

However, since Tang et al. of Eastman Kodak have made public an organic thin film electroluminescent device of a built-up structure having an amorphous luminescent or emission layer capable of realizing low voltage drive and high brightness emission in 1987, extensive studies have been made, in various fields, on the emission, stability, rise in brightness, built-up structure, manner of fabrication and the like with respect to the three primaries of R, G and B.

Furthermore, diverse novel materials have been prepared with the aid of the molecular design inherent to an organic material. At present, it starts to conduct extensive studies on applications, to color displays, of organic electroluminescent devices having excellent characteristic features of DC low voltage drive, thinning, and spontaneous light emission and the like.

The organic electroluminescent device (which may be sometimes referred to as organic EL device hereinafter) has a film thickness of 1 $\mu$m or below. When an electric current is charged to the device, the electric energy is converted to a light energy thereby causing luminescence to be emitted in the form of a plane. Thus, the device has an ideal feature for use as a display device of the spontaneous emission type.

FIG. 7 shows an example of a known organic EL device. An organic EL device 10 includes, on a transparent substrate 6 (e.g. a glass substrate), an ITO (indium tin oxide) transparent electrode 5, a hole transport layer 4, an emission layer 3, an electron transport layer 2, and a cathode 1 (e.g. an aluminium electrode) formed in this order, for example, by a vacuum deposition method.

A DC voltage 7 is selectively applied between the transparent electrode 5 serving as an anode and the cathode 1, so that holes serving as carriers charged from the transparent electrode 5 are moved via the hole transport layer 4, and electrons charged from the cathode 1 are moved via the electron transport layer 2, thereby causing the re-combination of the electrons-holes. From the site of the re-combination, light 8 with a given wavelength is emitted and can be observed from the side of the transparent substrate 6.

The emission layer 3 may be made of a light-emitting substance such as, for example, anthracene, naphthalene, phenanthrene, pyrene, chrysene, perylene, butadiene, coumarin, acridine, stilbene and the like. This may be contained in the electron transport layer 2.

FIG. 8 shows another example of an organic EL device. In an organic EL device 20, the emission layer 3 as in FIG. 7 is omitted and, instead, such a light-emitting substance as mentioned above is contained in the electron transport layer 2, and thus, the organic EL device 20 is so arranged as to emit light 18 having a given wavelength from an interface between the electron transport layer 2 and the hole transport layer 4.

FIG. 9 shows an application of the organic EL device. More particularly, a built-up body of the respective organic layers (including the hole transport layer 4, and the emission layer 3 or the electron transport layer 2) is interposed between the cathode 1 and the anode 5. These electrodes are, respectively, provided in the form of stripes that are intersected in the form of a matrix. In this state, a signal voltage is applied to in time series by means of a luminance signal circuit 34 and a shift register-built in control circuit 35 so that light is emitted at a number of intersected points (pixels), respectively.

Such an arrangement as set out above is usable not only as a display, but also as an image reproducing apparatus. It will be noted that if the striped pattern is provided for the respective colors of R, G and B, there can be obtained a full color or a multi-color arrangement.

In a display device made of a plurality of pixels using the organic EL device, emitting organic thin film layers 2, 3 and 4 are usually sandwiched between the transparent electrode 5 and the metal electrode 1, and emission occurs at the side of the transparent electrode 5.

For use as constituting materials of the organic EL device, attention has now been drawn to organic luminescent materials and carrier transport materials suitable for use in combination with the organic luminescent materials. The advantages of these organic materials reside in that their optical and electrical properties can be controlled to some extent through the molecular design thereof. When an organic luminescent material having a given light emission and a carrier transport material suited therewith are used in combination, efficient light emission is ensured. Accordingly, there can be realized a full color organic EL device wherein primaries of R, G and B are emitted using the respective luminescent materials.

In some case, such an organic EL device as set out above may have such a structure that a hole transport layer serves also as a luminescent element. In this device structure, it is essential to provide a carrier transport layer that is able to efficiently transport electrons and block holes. However, organic materials that satisfy the above requirement and the efficient manufacture of these materials have never been found yet.

SUMAMRY OF THE INVENTION

An object of the invention is to provide a novel organic material, which is suitable for use as a carrier transport material capable of efficiently transporting electrons and blocking holes.

Another object of the invention is to provide a process for preparing such an organic compound as mentioned above in an efficient manner.

According to an aspect of the invention, there is provided a bathophenanthroline compound of the following general formula [I] or [II]

Formula (I)]:

General Formula [I]

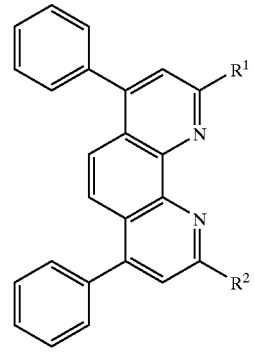

wherein $R^1$ and $R^2$ may be the same or different and independently represent hydrocarbon group provided that at least one of $R^1$ and $R^2$ has at least two carbons, or General Formula [II]:

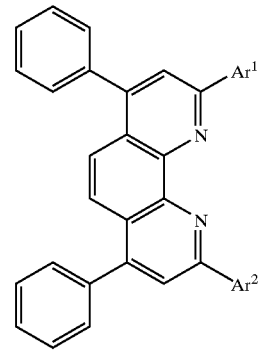

wherein $Ar^1$ and $Ar^2$ may be the same or different and independently represent an aryl group. The hydrocarbon group may be linear, branched or cyclic, saturated or unsaturated, or substituted or unsubsituted. Further, the aryl group may also be substituted or unsubstituted.

The bathophenanthroline compound of the invention can control carrier transportability depending on the type of substituent introduced into the molecule, and can thus be utilizable as a carrier transport material of various types of organic EL devices. The compounds have high glass transition point and high melting point and are stable electrically, thermally and/or chemically. In addition, the compounds are sublimable in nature, which is advantageous in that a uniform amorphous film can be readily formed according to a vacuum deposition process.

In the bathophenanthroline compounds of the formulas [I] and [II], it is preferred that $R^1$ and $R^2$, and $Ar^1$ and $Ar^2$ are, respectively, the same. It will be noted that the term "aryl group" used herein means a carbocyclic aromatic group such as, for example, a phenyl group, a naphthyl group, an anthryl group or the like, and a heterocyclic aromatic group such as, for example, a furyl group, a thienyl group, a pyridyl group or the like.

According to another aspect of the invention, there is also provided a process for preparing a bathophenanthroline compound comprising subjecting a lithium compound of the following general formula (III) or (V).

General Formula (III):

$R^1$—Li or $R^2$—Li wherein $R^1$ and $R^2$ may be the same or different and independently represent a hydrocarbon group provided that at least one of $R^1$ and $R^2$ has at least two carbon atoms, or General Formula (V):

$Ar^1$—Li or $Ar^2$—Li wherein $Ar^1$ and $Ar^2$ may be the same or different and independently represent an aryl group, and bathophenanthroline of the following structural formula (IV)

Structural Formula (IV):

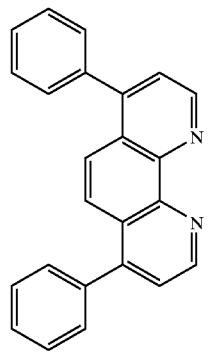

to nucleophilic substitution reaction to obtain a bathophenanthroline compound of the afore-indicated formula (I) or (II). The hydrocarbon group may be linear, branched or cyclic, saturated or unsaturated, or substituted or unsubsituted. Further, the aryl group may also be substituted or unsubstituted.

According to the preparation process of the invention, the bathophenanthroline compound of the invention can be efficiently prepared. It is preferred that in the course of the nucleophilic substitution reaction, carbanions are generated from the lithium compound and subsequently reacted with the bathophenanthroline.

BRIEF DESCRIPTION OF THE DRAWINGS

FIG. 3 is a schematic sectional view showing a vacuum deposition apparatus used to make the organic EL device;

FIG. 9 is a schematic perspective view showing an example of further another type of prior-art organic EL device.

DETAILED DESCRIPTION OF THE PREFERRED EMBODIMENTS

Figure 1:
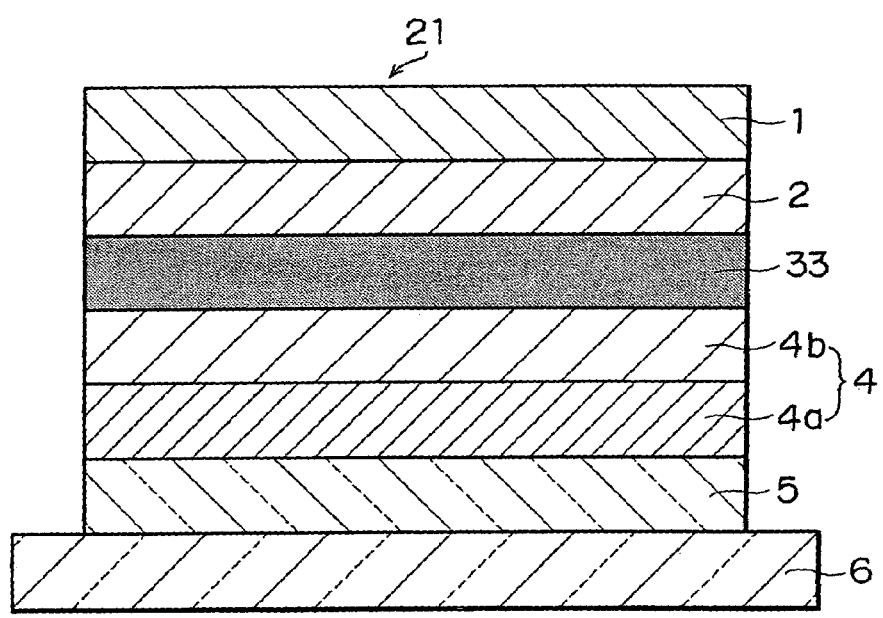
FIG. 1 is a schematic sectional view showing an essential part of an organic EL device using a bathophenanthroline compound of the invention.

The bathophenanthroline compound of the invention is described in more detail. In the compound of the general formula [I], $R^1$ and $R^2$ independently represent a linear, branched or cyclic, saturated or unsaturated hydrocarbon group. Specific examples include an ethyl group, a butyl group, an n-propyl group, an isopropyl group, an n-butyl group, a sec-butyl group, a tert-butyl group, an n-pentyl group, an iso-pentyl group, a neopentyl group, a tert-pentyl group, a cyclopentyl group, an n-hexyl group, a 2-ethylbutyl group, a 3,3-dimethylbutyl group, a cyclohexyl group, an n-heptyl group, a cyclohexylmethyl group, an n-octyl group, a tert-octyl group, a 2-ethylheyxl group, an n-nonyl group, an n-decyl group, an n-dodecyl group, an n-tetradecyl group, an n-hexadecyl group and the like although not limited to those mentioned above.

Specific examples of the substituted or unsubstituted, saturated and unsaturated hydrocarbon group for $R^1$ and $R^2$ include a benzyl group, a phenethyl group, an α-methylbenzyl group, an α,α-dimethylbenzyl group, a 1-naphthylmethyl group, a 2-naphthylmethyl group, a furfuryl group, a 2-methylbenzyl group, a 3-methylbenzyl group, a 4-methylbenzyl group, a 4-ethylbenzyl group, a 4-isopropylbnezyl group, a 4-tert-butylbenzyl group, a 4-n-hexylbenzyl group, a 4-nonylbenzyl group, a 3,4-dimethylbenzyl group, and the like saturated or unsaturated hydrocarbon group although not limited to those mentioned above.

In the general formula [II], $Ar^1$ and $Ar^2$ independently represent a substituted or unsubstituted aryl group. Specific examples include a phenyl group, a 1-naphthyl group, a 2-anthryl group, a 9-anthryl group, a 2-fluorenyl group, a 4-quinolyl group, a pyridyl group, a 3-pyridynyl group, a 2-pyridynyl group, a 3-furyl group, a 2-furyl group, a 3-thienyl group, a 2-oxazolyl group, a 2-thiazolyl group, a 2-benzoxazoryl group, a 2-benzothiazoryl group, a 2-benzoimidazoryl group, a 4-methylphenyl group, a 3-methylphenyl group, a 2-methylphenyl group, a 2,3-dimethylphenyl group, a 2,4-dimethylphenyl group, a 2,5-dimethylphenyl group, a 2,6-dimethylphenyl group, a 3,4-dimethylphenyl group, a, 3,5-diemthylphenyl group, a 2,3,4-trimethylphenyl group, a 2,3,5-trimethylphenyl group, a 2,3,6-trimethylphenyl group, a 3,4,5-trimethylphenyl group, a 4-ethylphenyl group, a 3-ethylphenyl group, a 2-ethylphenyl group, a 2,3-diethylphenyl group, a 2,4-diethylphenyl group, a 2,5-diethylphenyl group, a 2,6-diethylphenyl group, a 3,4-diethylphenyl group, a 3,5-diethylphenyl group, a 2,3,4-triethylphenyl group, a 2,3,5-triethylphenyl group, a 2,3,6-triethylphenyl group, a 3,4,5-triethylphenyl group, a 4-n-propylphenyl group, a 4-isopropylphenyl group, a 2-isopropylphenyl group, a 4-n-butylphenyl group, a 4-isobutylphenyl group, a 4-sec-butylphenyl group, a 4-tert-butylphenyl group, a 3-tert-butlphenyl group, a 2-tert-butylphenyl group and the like although not limited to those mentioned above.

Specific examples of the bathophenanthroline compound of the invention includes those mentioned below as Compound Nos. 1 to 178, but these compounds should not be construed as limitation thereof. In the specific compounds, Me represents a methyl group, Et represents an ethyl group, Pr represents a propyl group, and Bu represents a butyl group.

Compound No. 1

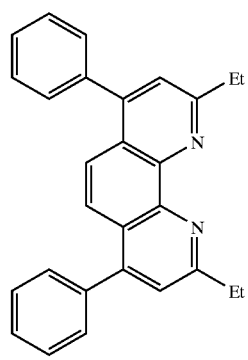

Compound No.2

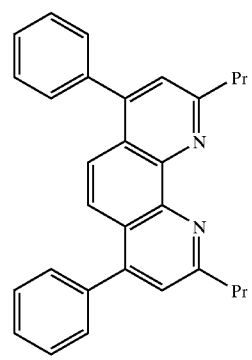

Compound No.3

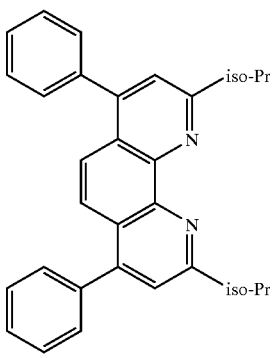

-continued

Compound No. 4

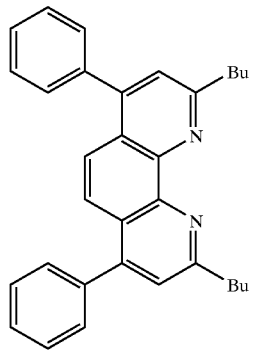

Compound No. 5

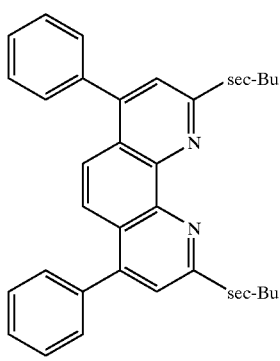

Compound No. 6

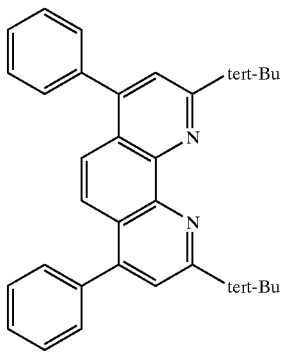

Compound No.7

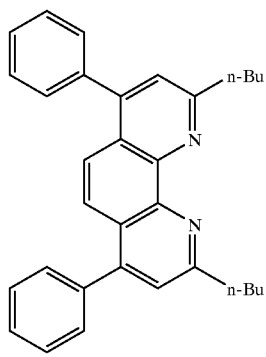

-continued
Compound No.8
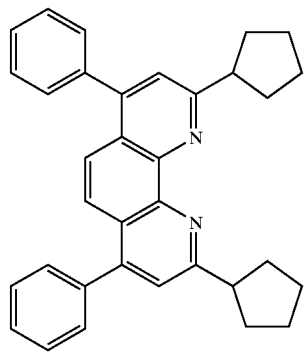
Compound No. 9
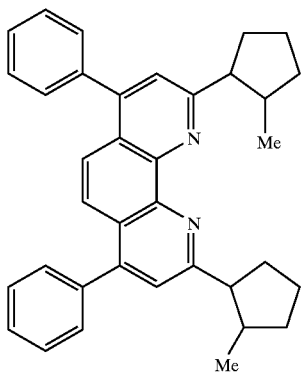
Compound No. 10
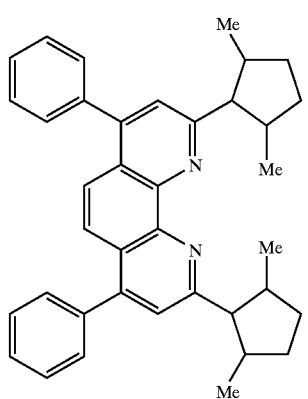
Compound No.11
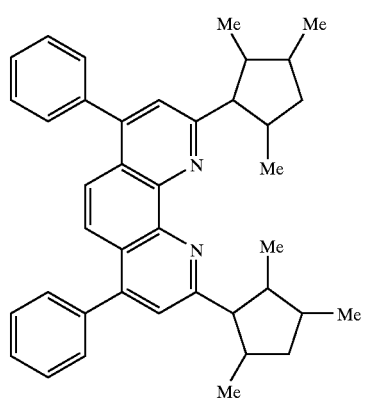
-continued
Compound No. 12
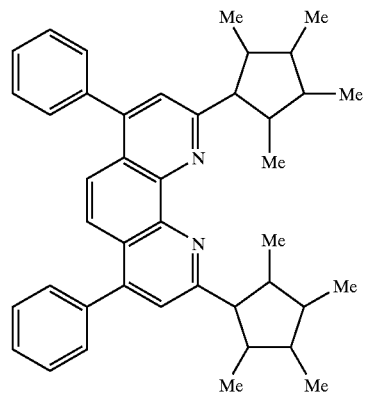
Compound No. 13
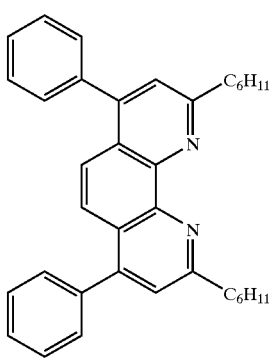
Compound No.14
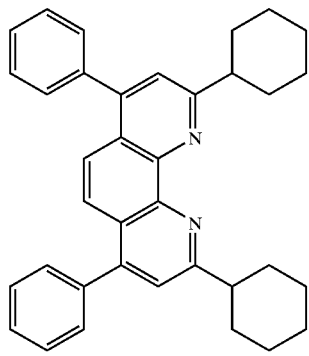
Compound No.15
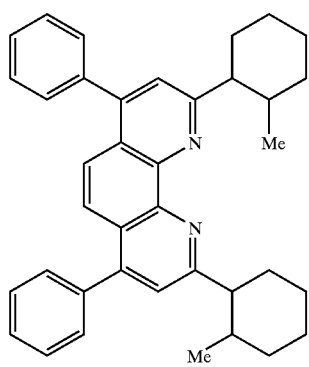

-continued
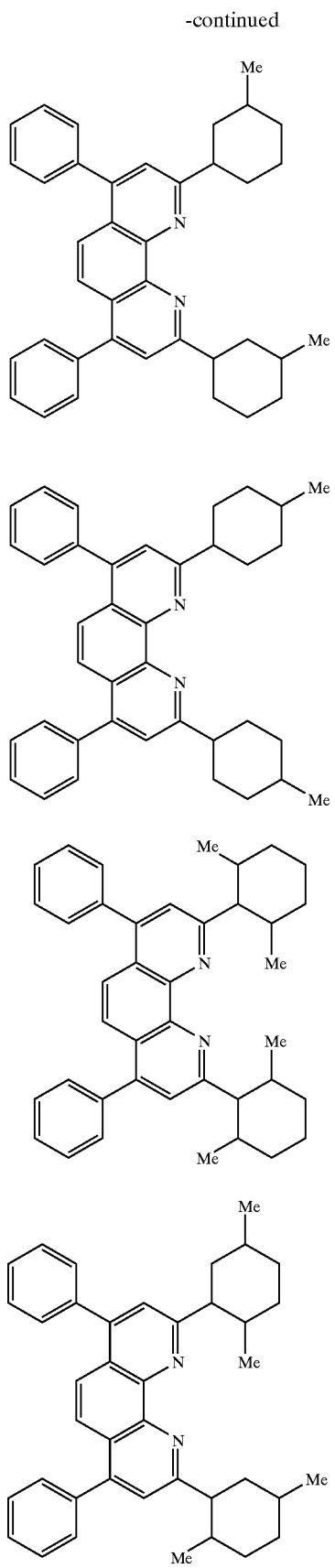
Compound No.16
Compound No.17
Compound No.18
Compound No. 19
-continued
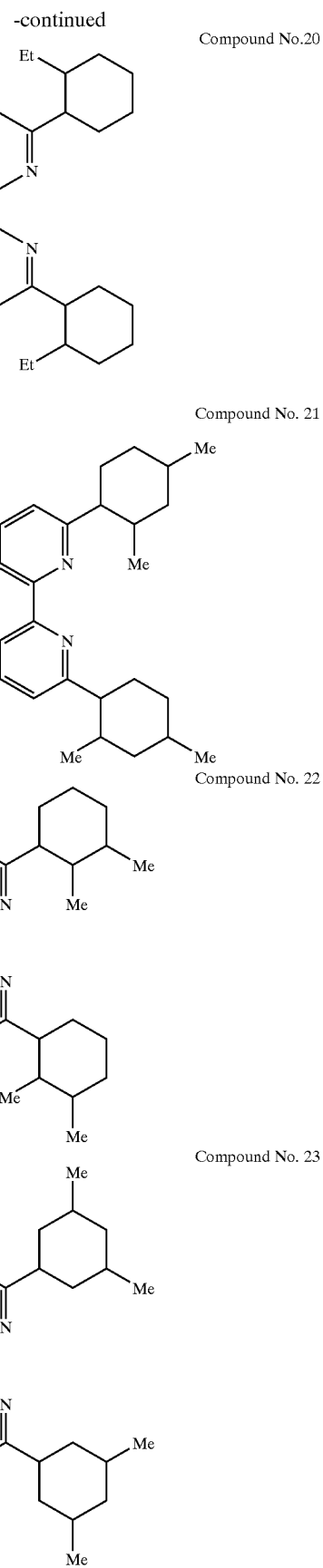
Compound No.20
Compound No. 21
Compound No. 22
Compound No. 23

-continued
Compound No.24
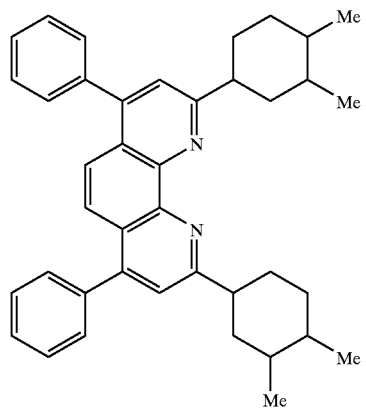
Compound No. 25
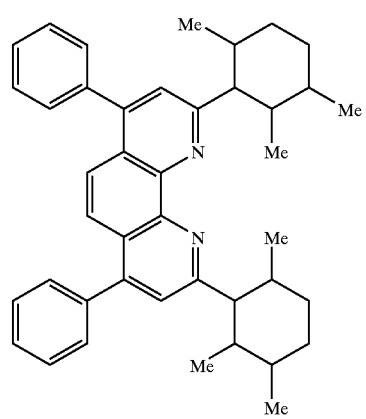
Compound No. 26
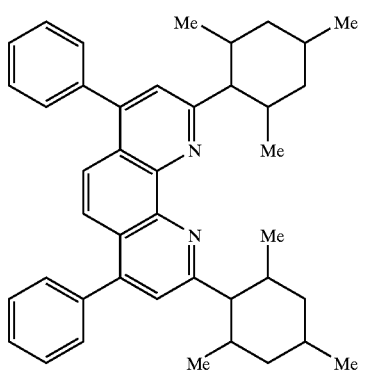
Compound No. 27
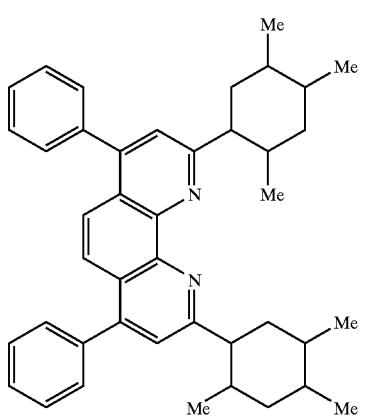
Compound No.28
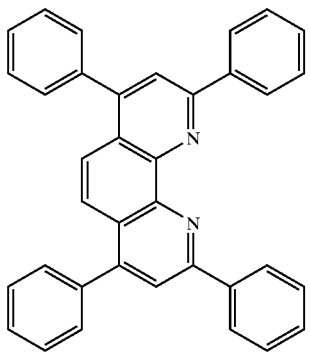
Compound No. 29
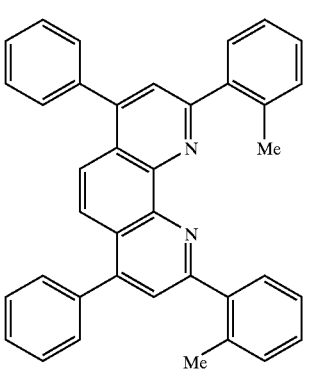
Compound No. 30
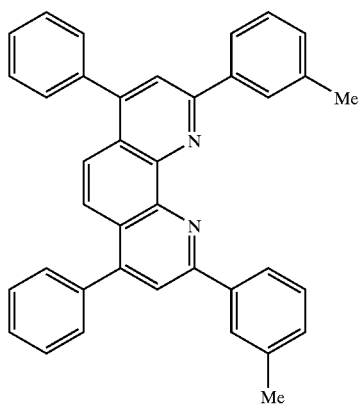
Compound No. 31
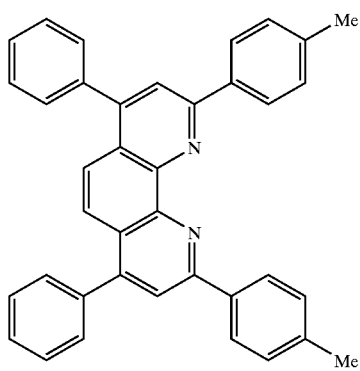

-continued
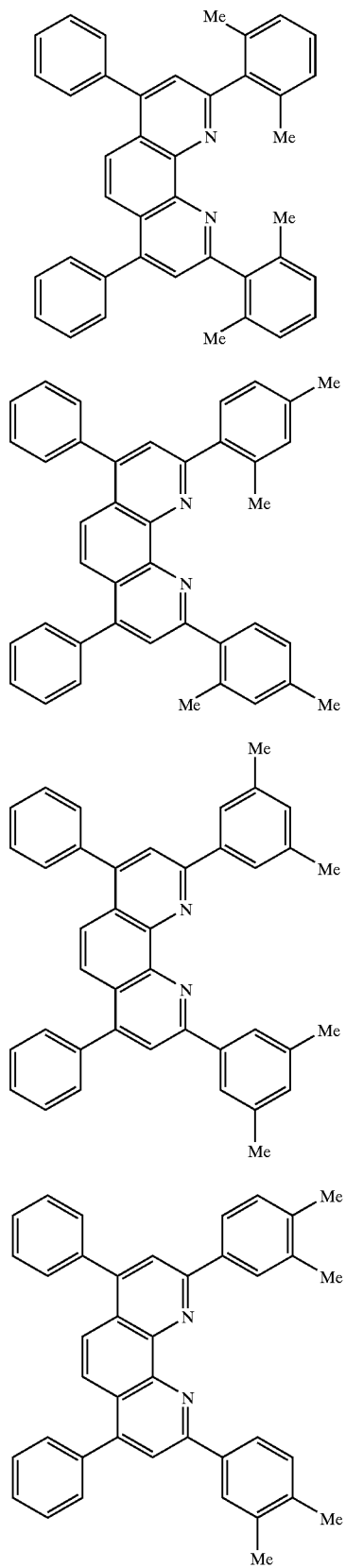
Compound No. 32
Compound No. 33
Compound No. 34
Compound No.35
-continued
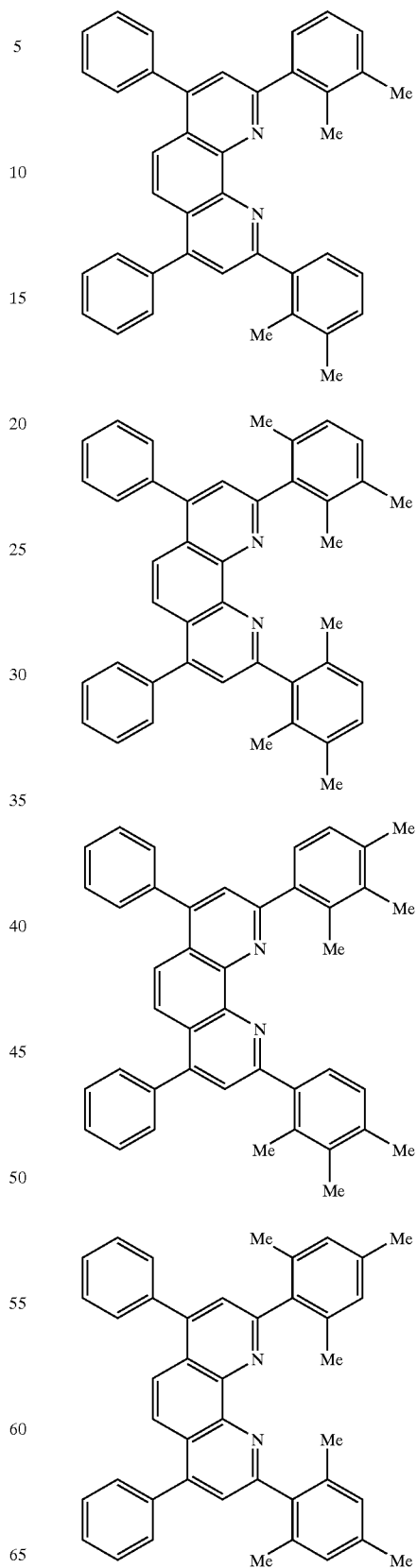
Compound No. 36
Compound No. 37
Compound No.38
Compound No. 39

-continued
Compound No. 40
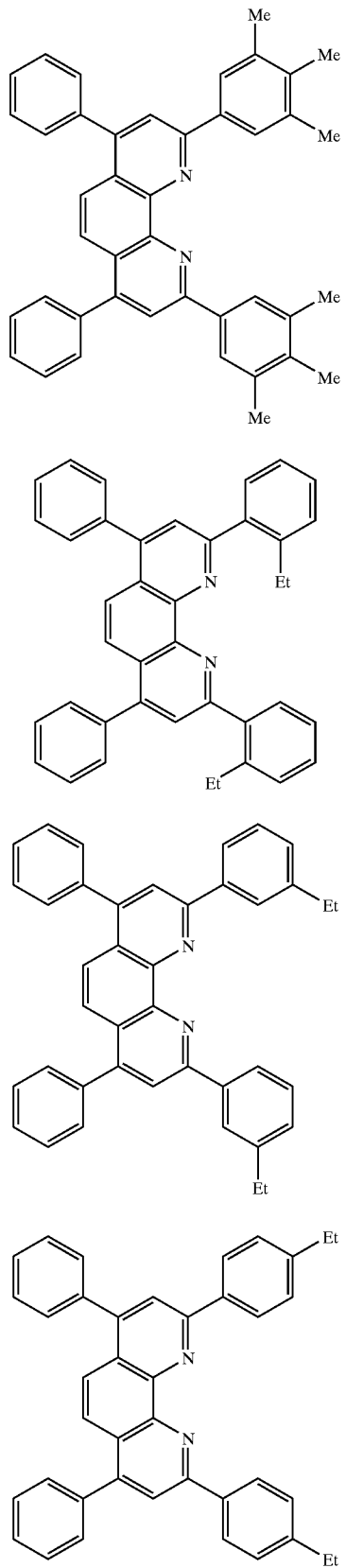
Compound No. 41
Compound No. 42
Compound No. 43
Compound No. 44
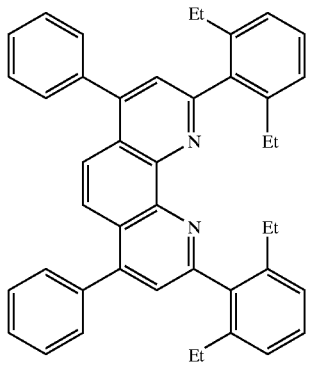
Compound No. 45
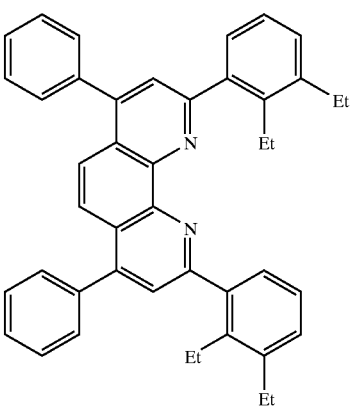
Compound No. 46
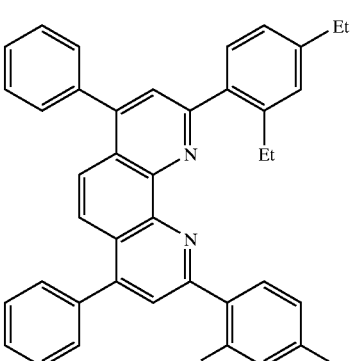
Compound No. 47
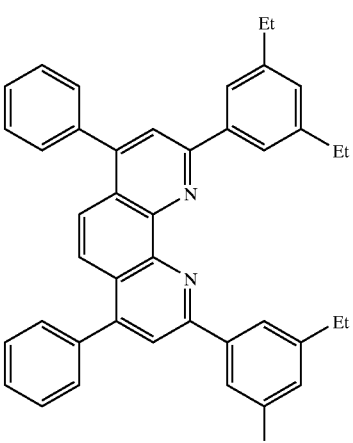

-continued
Compound No. 48
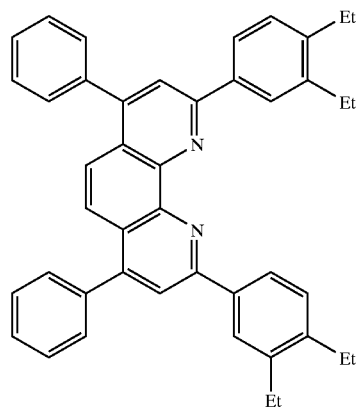
Compound No. 49
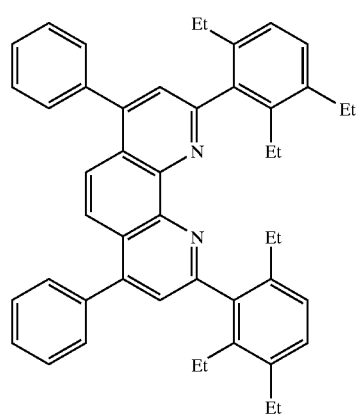
Compound No. 50
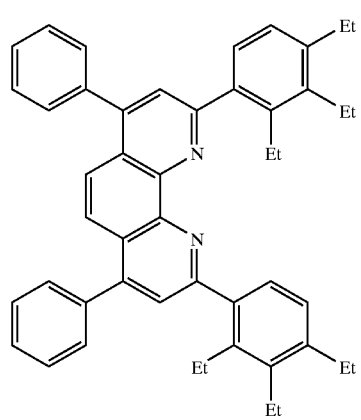
Compound No. 51
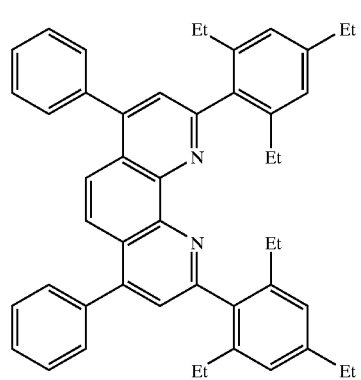
-continued
Compound No. 52
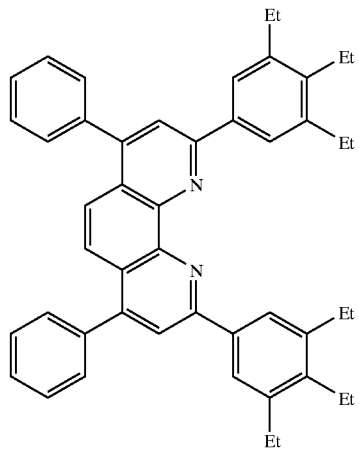
Compound No. 53
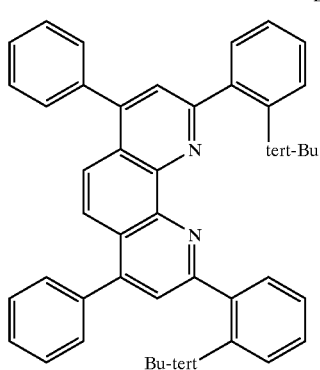
Compound No. 54
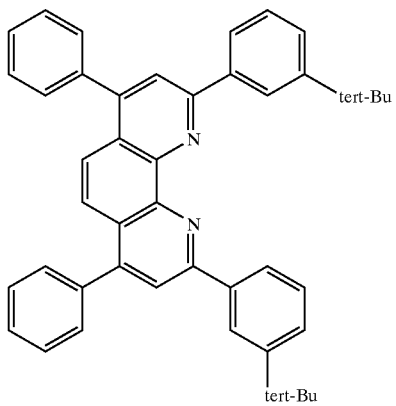
Compound No. 55
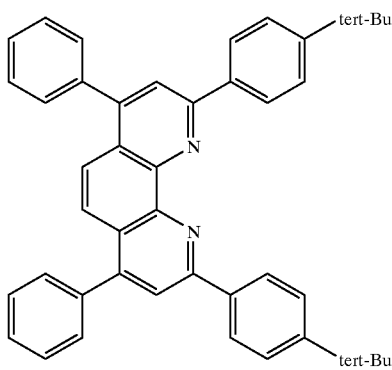

-continued
Compound No. 56
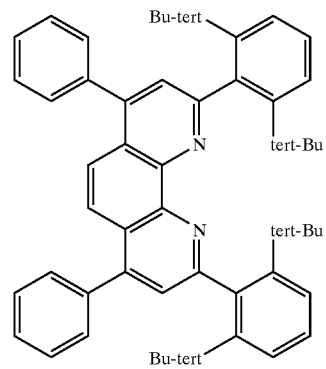
Compound No. 57
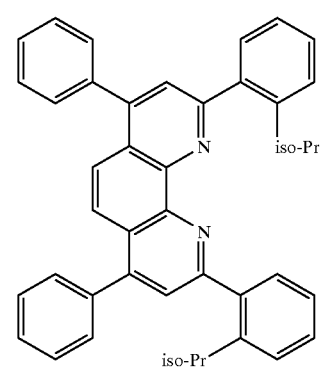
Compound No. 58
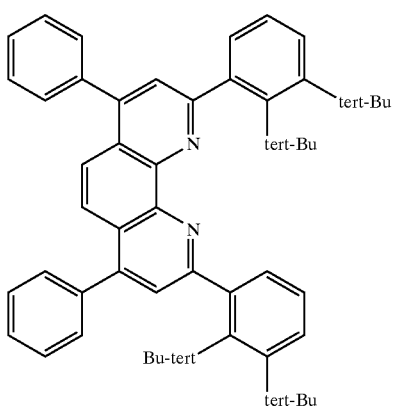
Compound No. 59
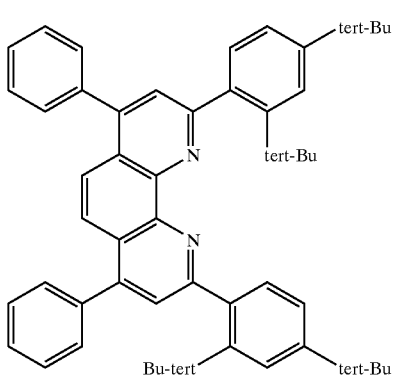
-continued
Compound No. 60
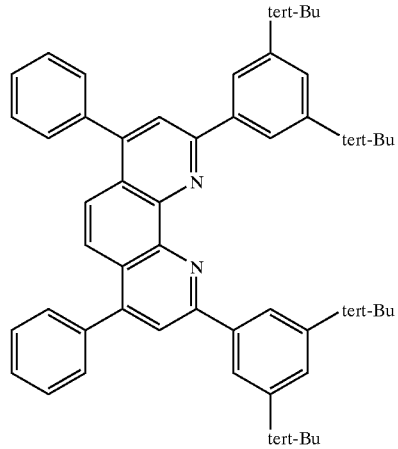
Compound No. 61
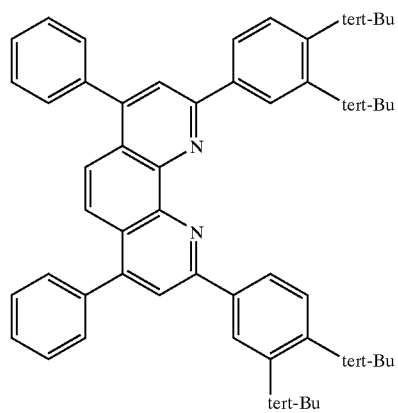
Compound No. 62
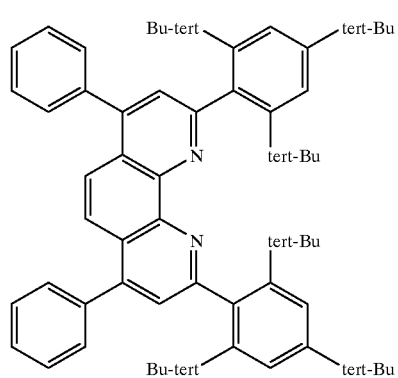

-continued
Compound No. 63
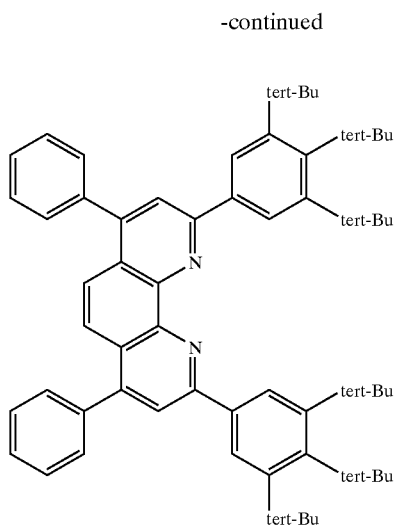
Compound No. 64
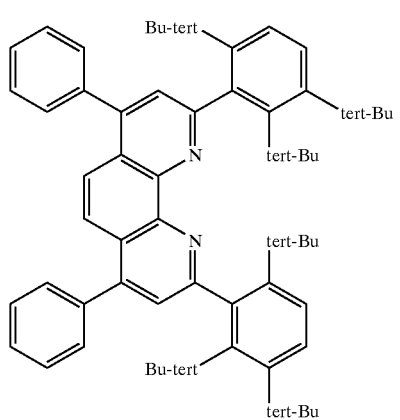
Compound No. 65
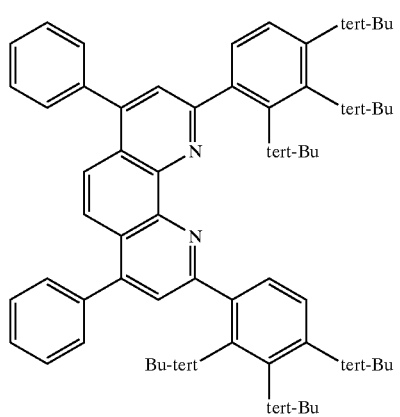
-continued
Compound No. 66
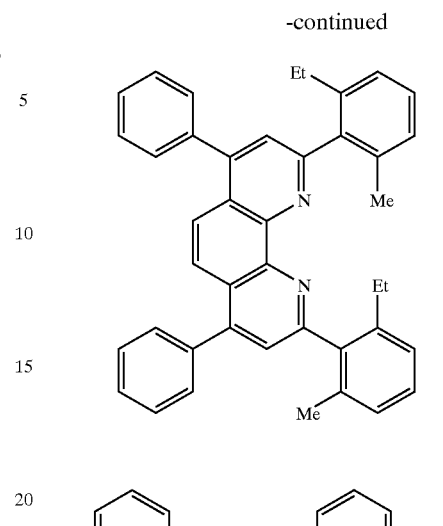
Compound No. 67
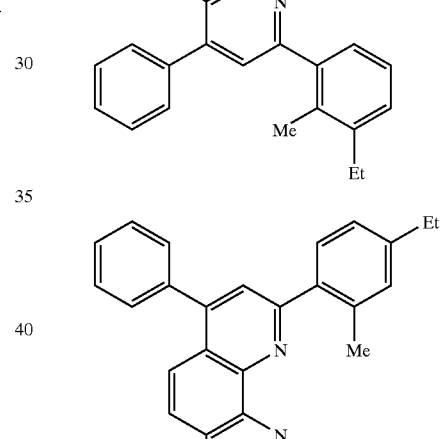
Compound No. 68
Compound No. 69
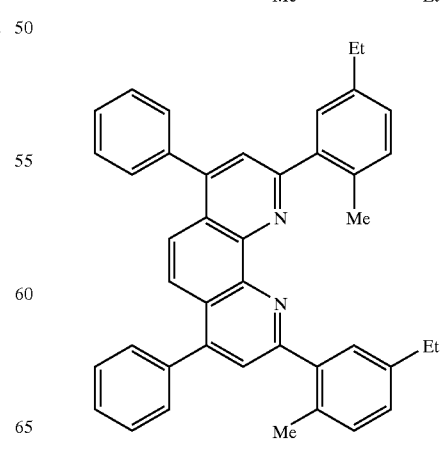

-continued
Compound No. 70
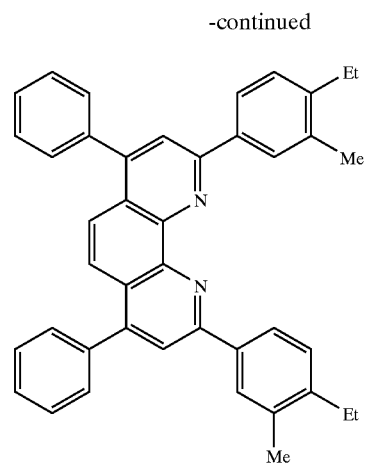
Compound No. 71
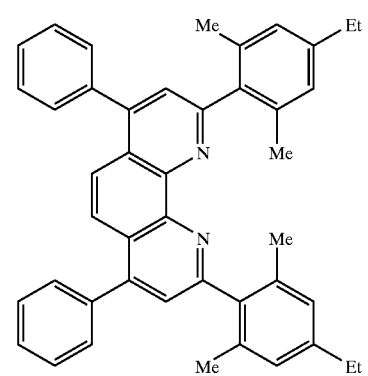
Compound No. 72
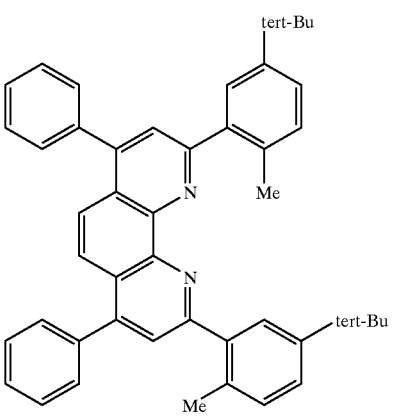
Compound No. 73
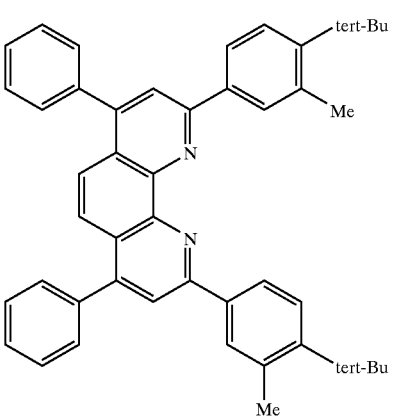
-continued
Compound No. 74
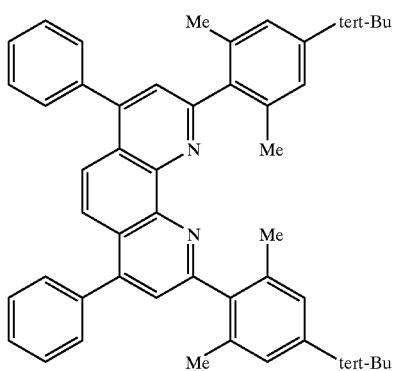
Compound No. 75
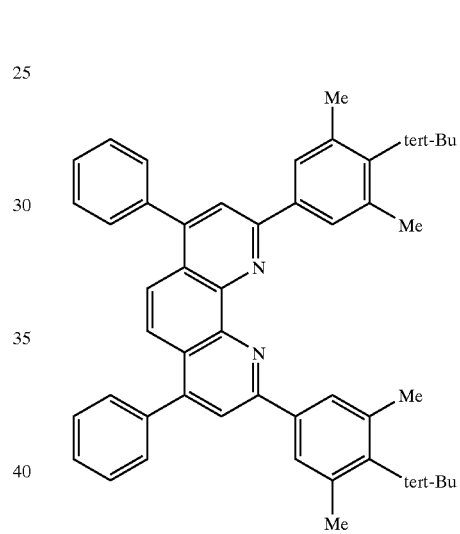
Compound No. 76
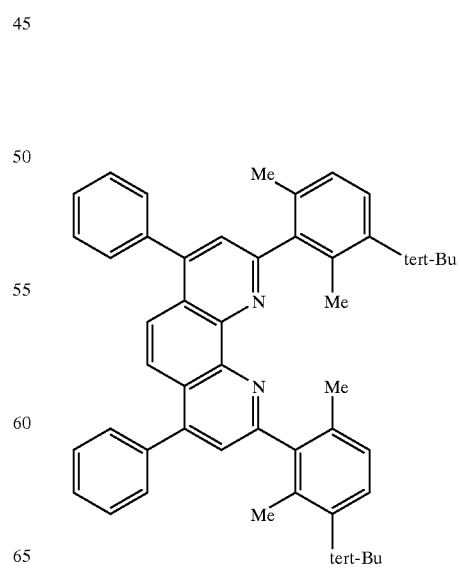

Compound No. 77
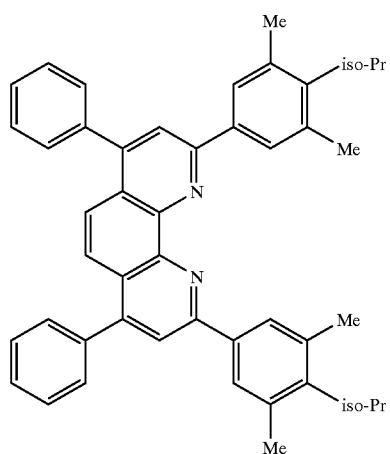
Compound No. 80
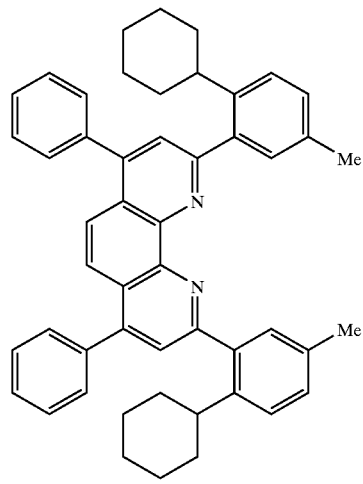
Compound No. 78
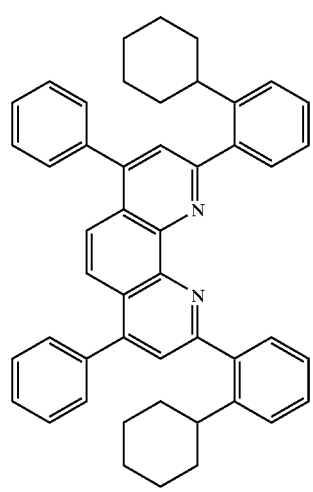
Compound No. 81
Compound No. 79
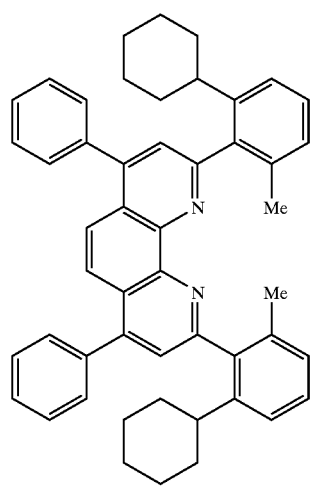
Compound No. 82
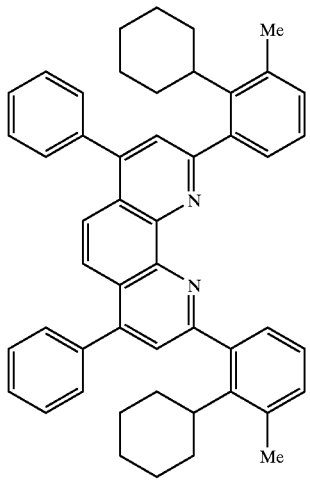

-continued
Compound No. 83
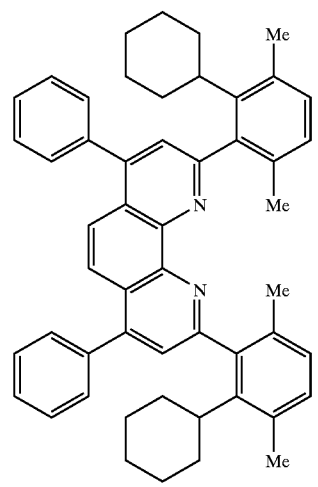
Compound No. 84
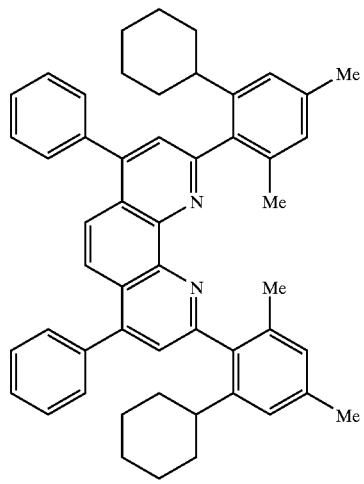
Compound No. 85
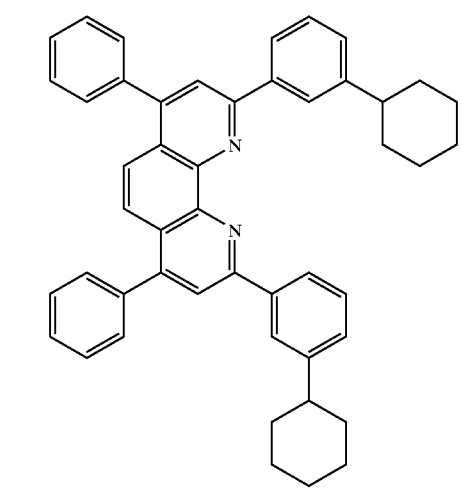
Compound No. 86
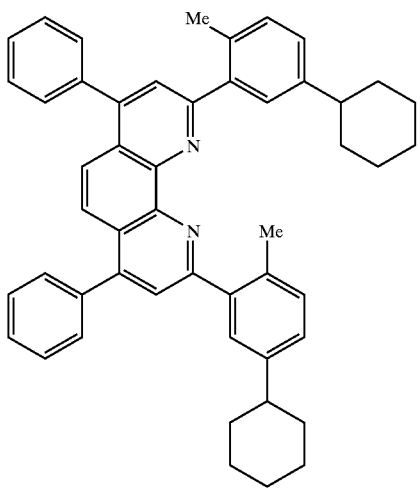
Compound No. 87
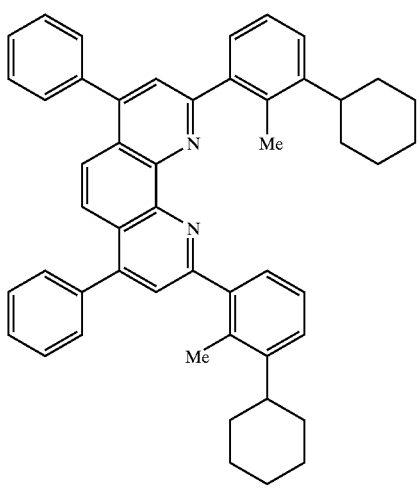
Compound No. 88
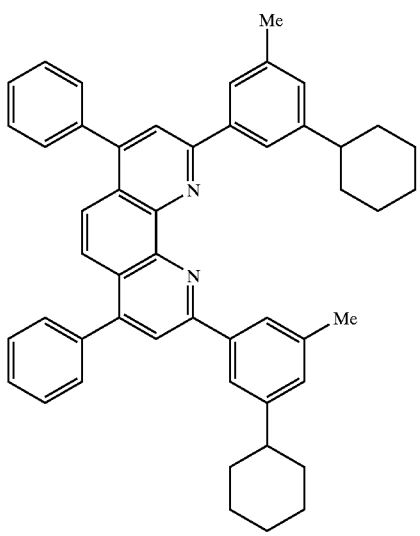

-continued
Compound No. 89
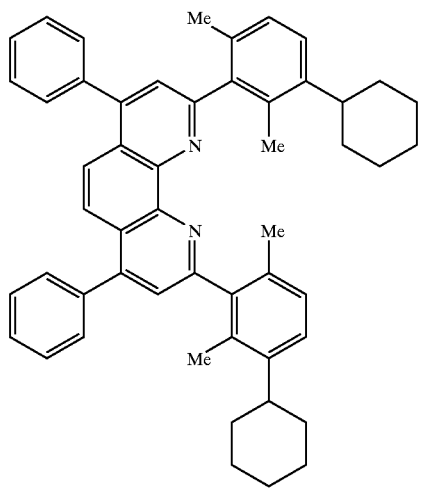
Compound No. 90
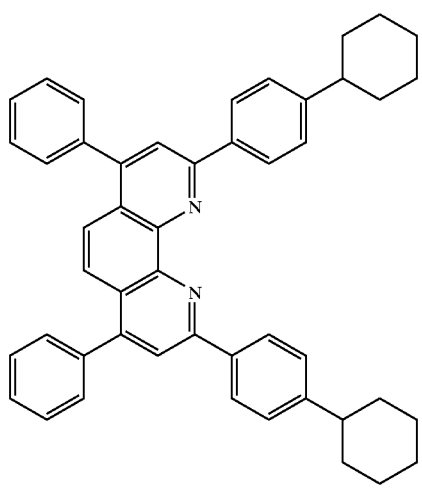
Compound No. 91
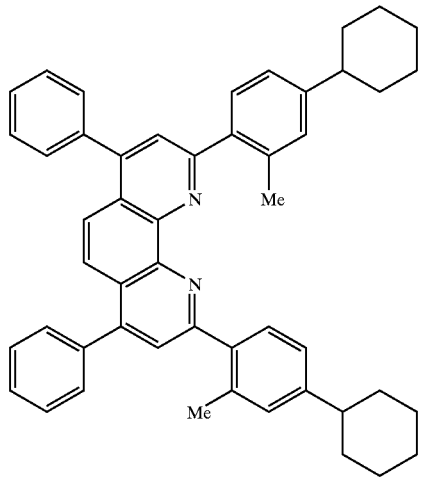
-continued
Compound No. 92
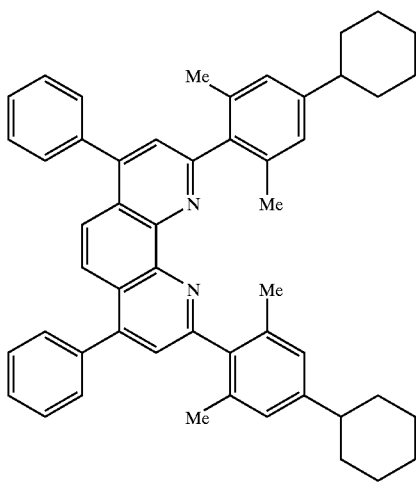
Compound No. 93
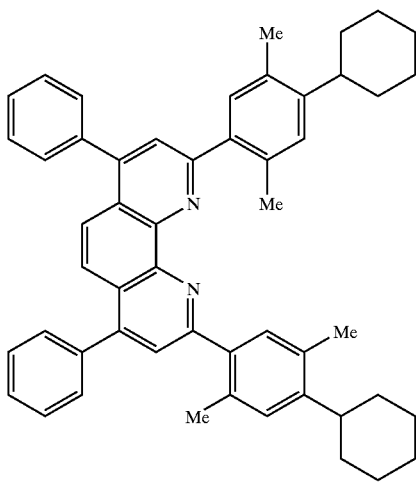
Compound No. 94
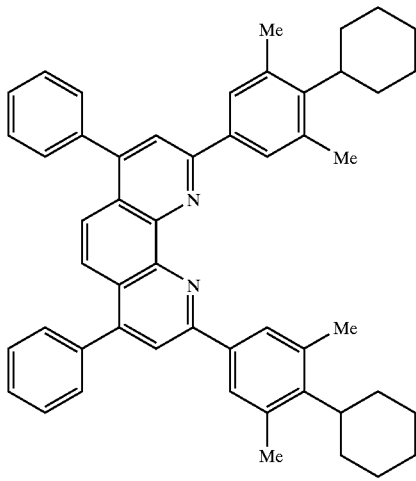

Compound No. 95
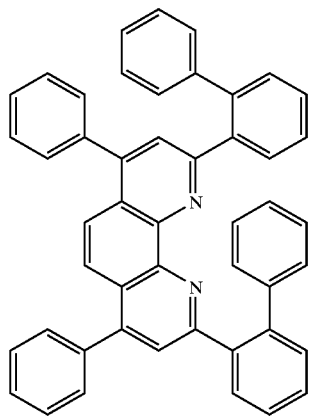
Compound No. 98
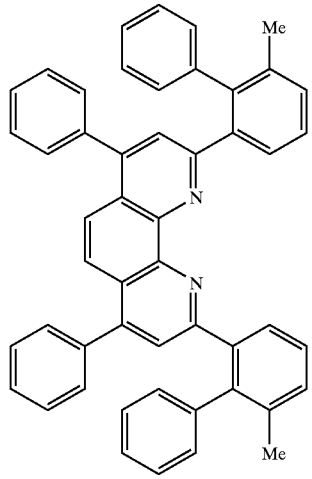
Compound No. 96
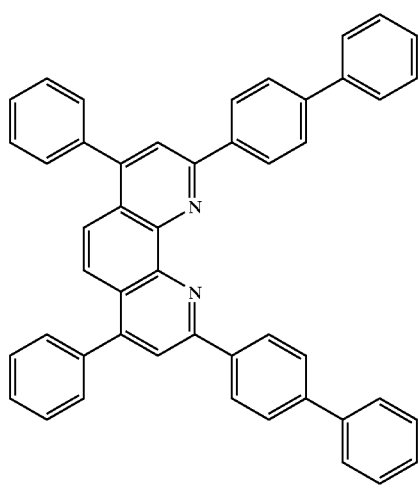
Compound No. 99
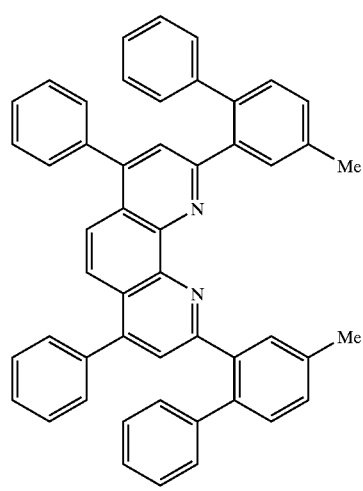
Compound No. 97
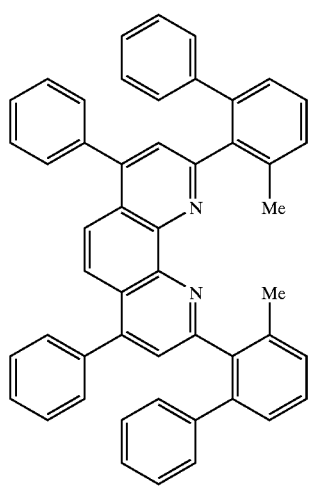
Compound No. 100
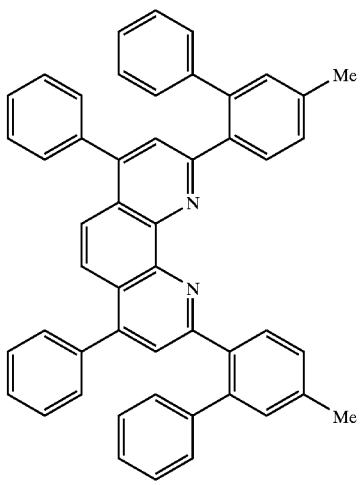

-continued
Compound No. 101
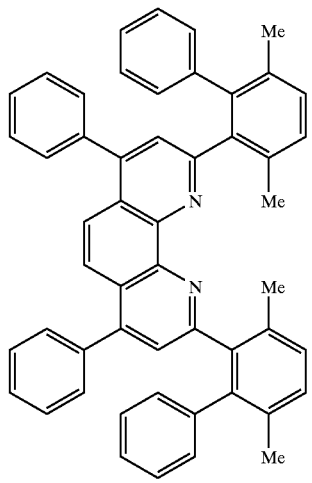
Compound No. 102
Compound No. 103
-continued
Compound No. 104
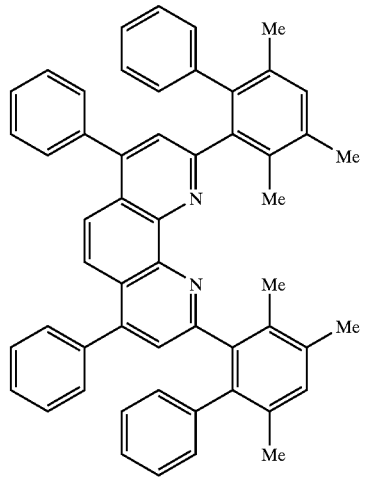
Compound No. 105
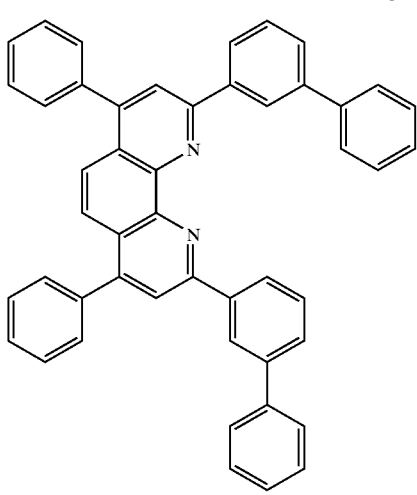
Compound No. 106
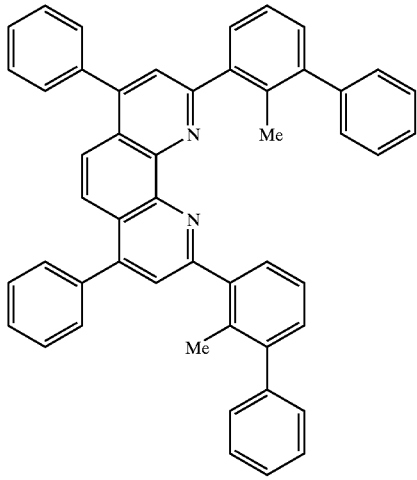

-continued
Compound No. 107
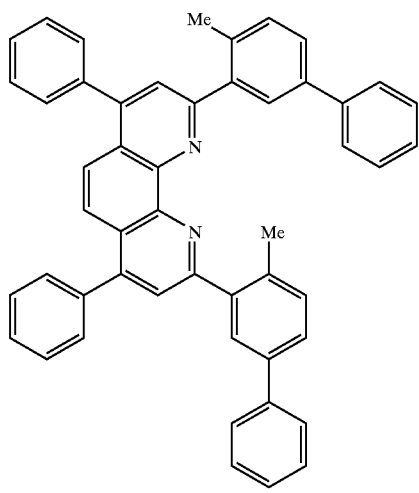
Compound No. 108
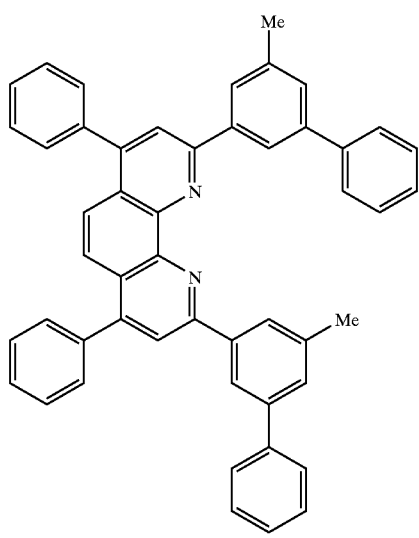
Compound No. 109
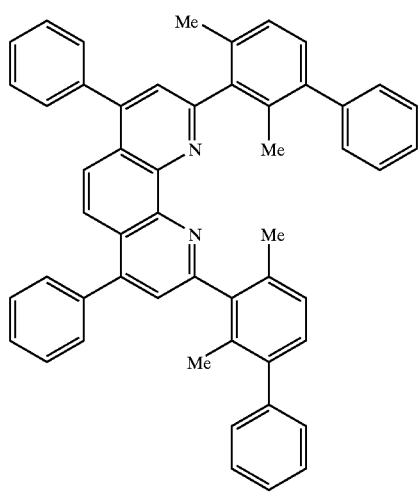
-continued
Compound No. 110
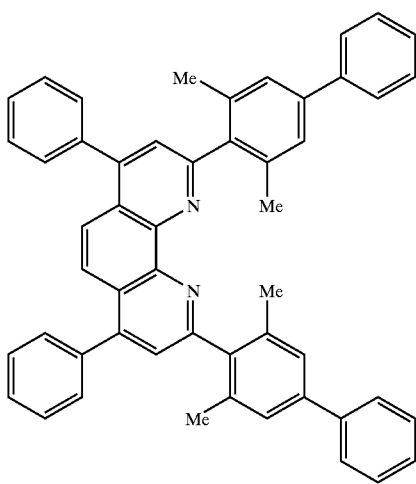
Compound No. 111
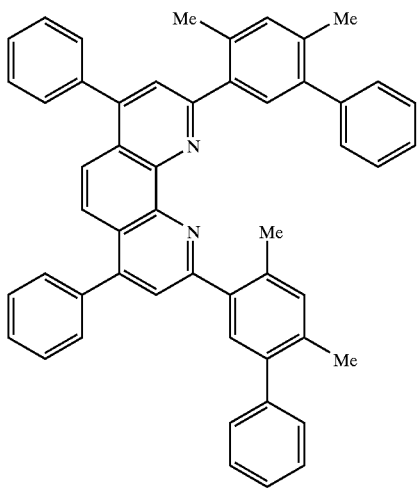
Compound No. 112
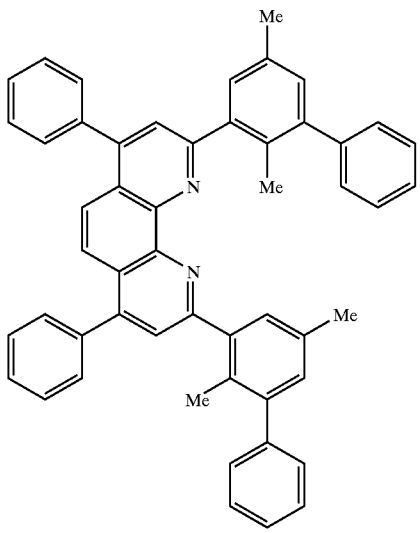

-continued
Compound No. 113
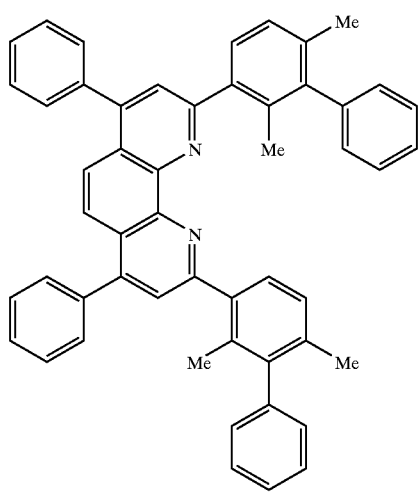
Compound No. 114
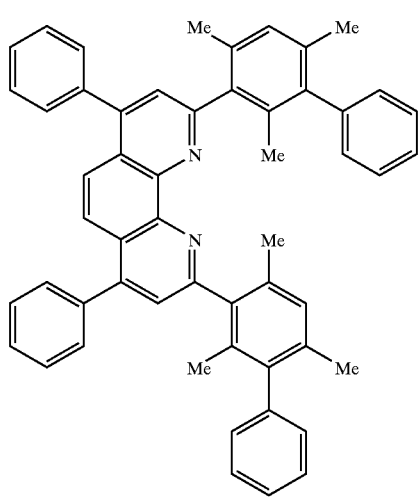
Compound No. 115
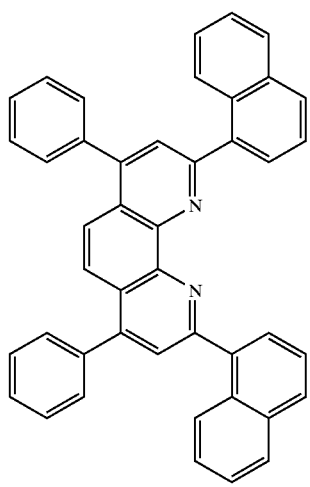
-continued
Compound No. 116
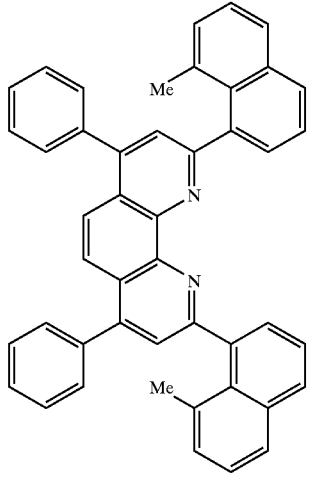
Compound No. 117
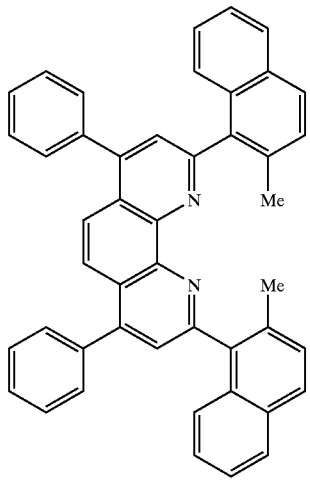
Compound No. 118
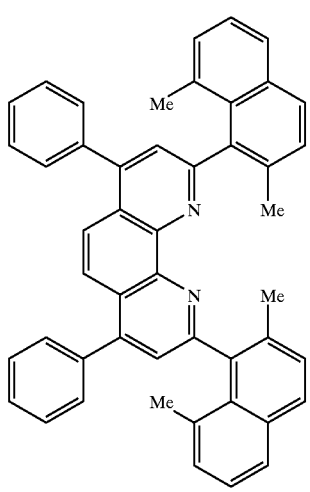

-continued
Compound No. 119
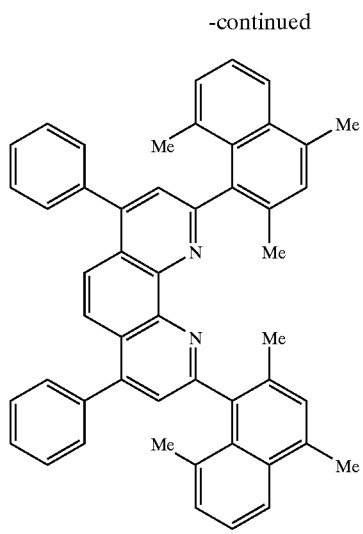
Compound No. 120
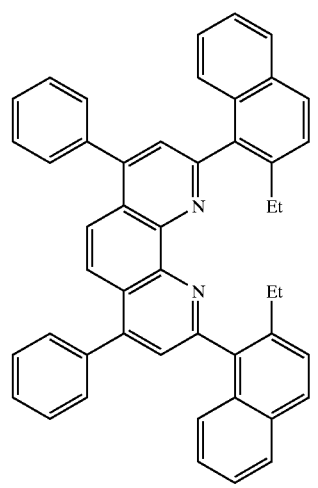
Compound No. 121
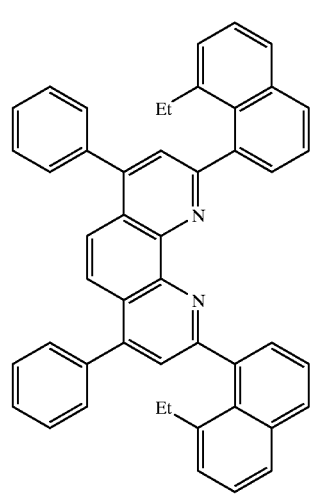
-continued
Compound No. 122
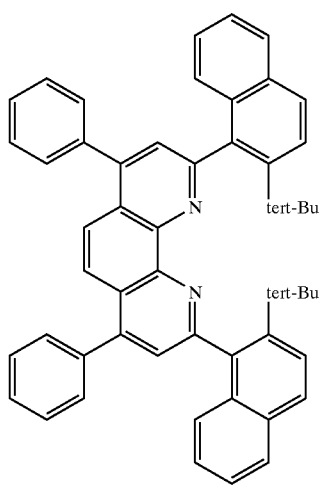
Compound No. 123
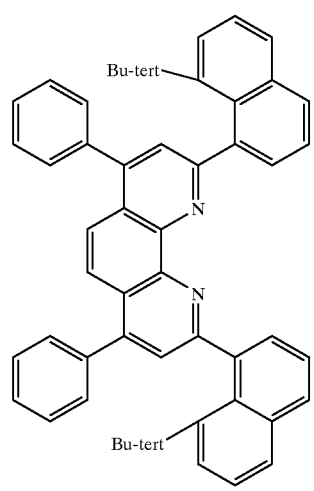
Compound No. 124
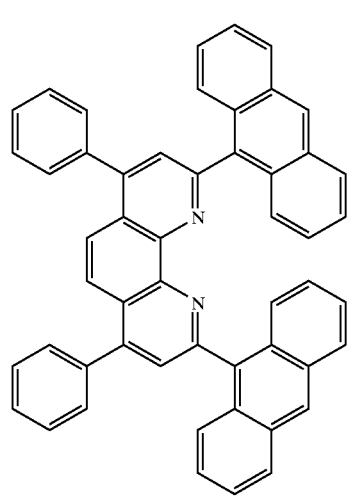

-continued
Compound No. 125
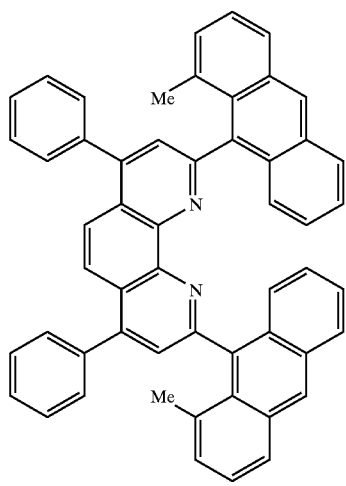
Compound No. 126
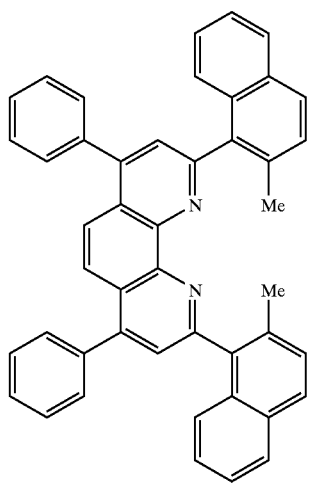
Compound No. 127
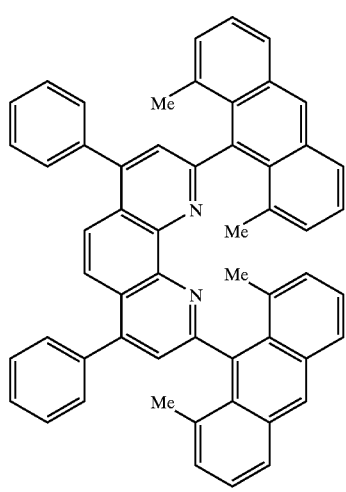
Compound No. 128
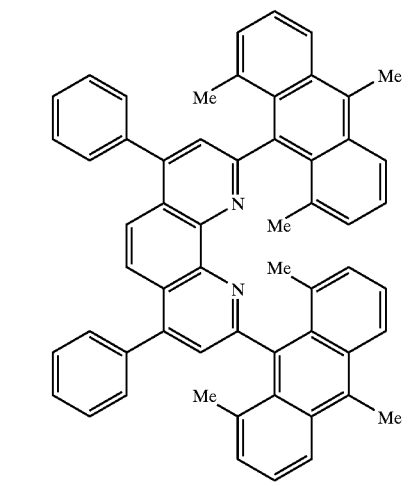
Compound No. 129
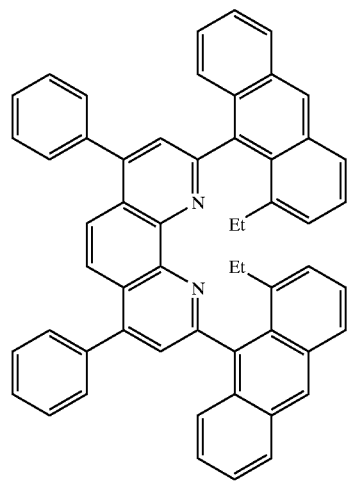
Compound No. 130
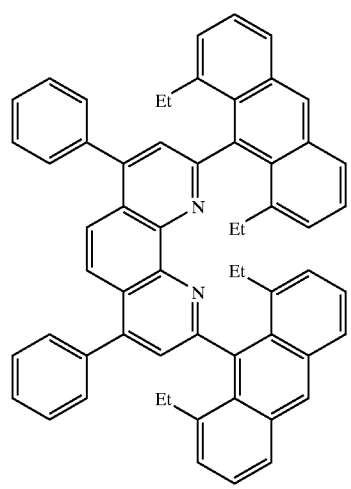

Compound No. 131
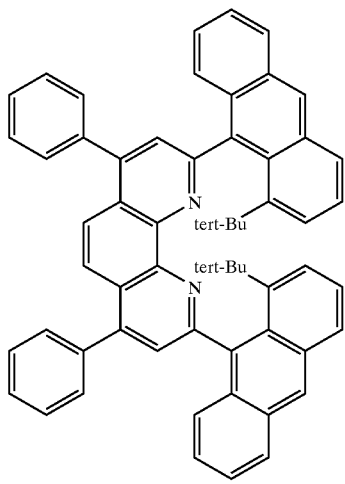
Compound No. 134
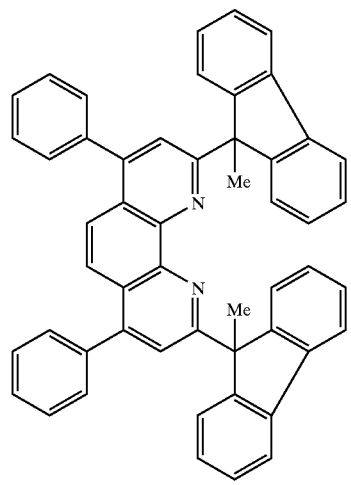
Compound No. 132
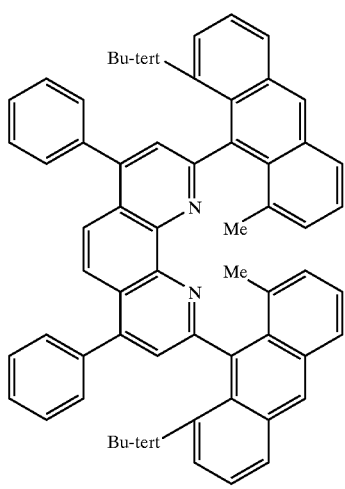
Compound No. 135
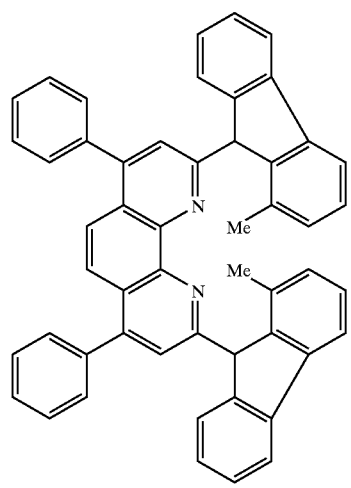
Compound No. 133
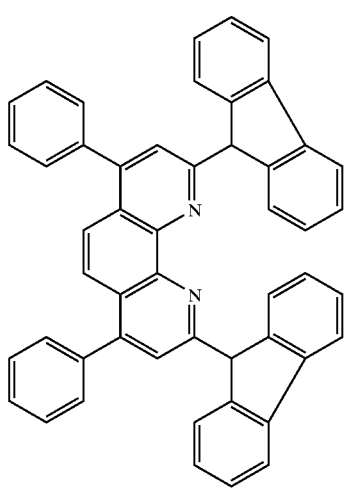
Compound No. 136
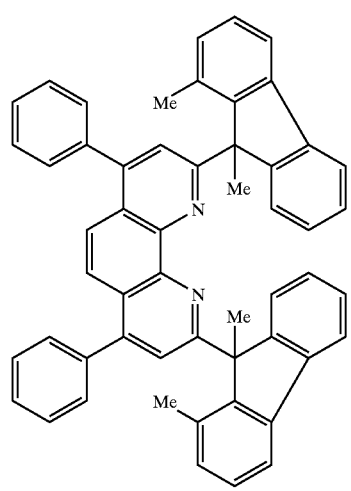

-continued
Compound No. 137
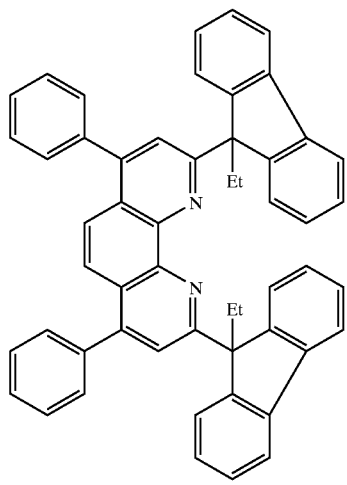
Compound No. 138
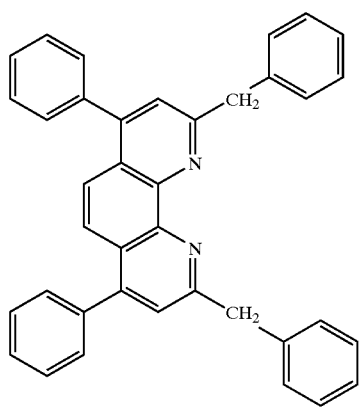
Compound No. 139
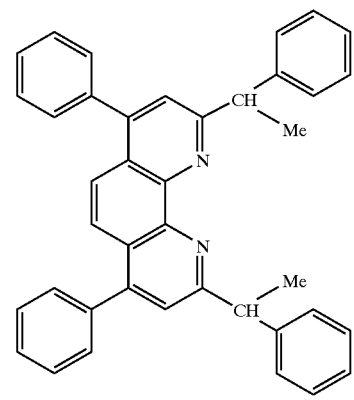
-continued
Compound No. 140
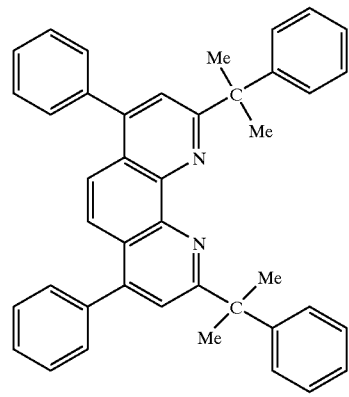
Compound No. 141
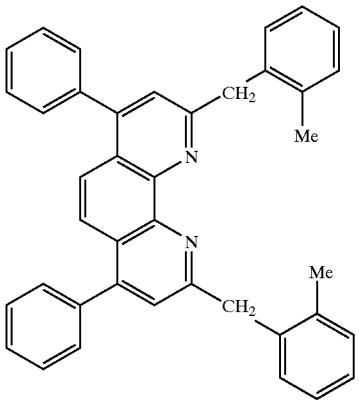
Compound No. 142
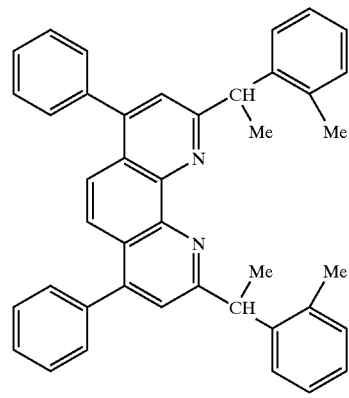
Compound No. 143
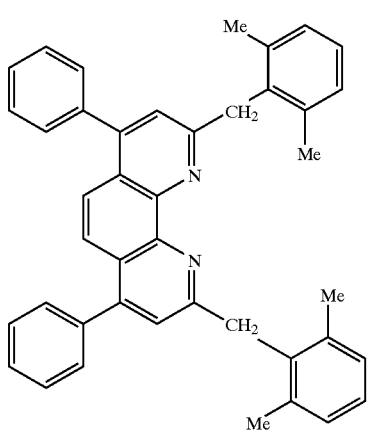

-continued
Compound No. 144
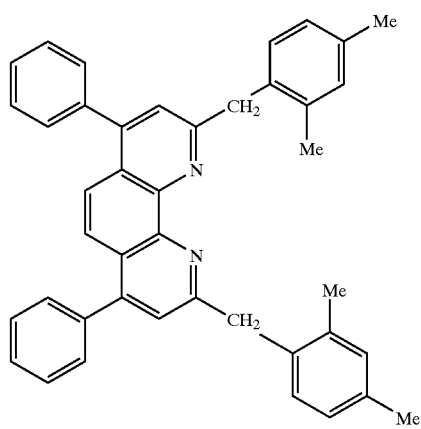
Compound No. 147
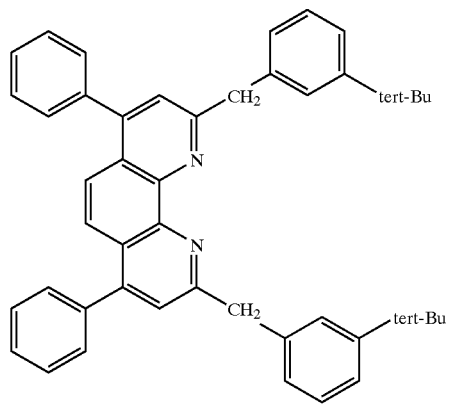
Compound No. 145
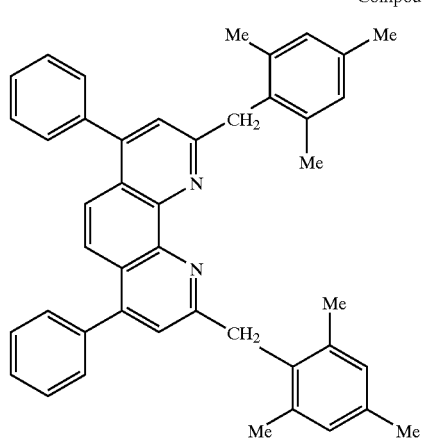
Compound No. 148
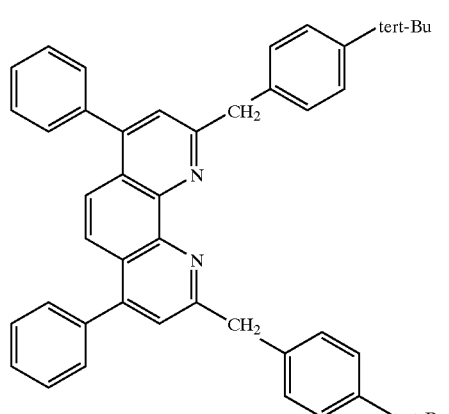
Compound No. 146
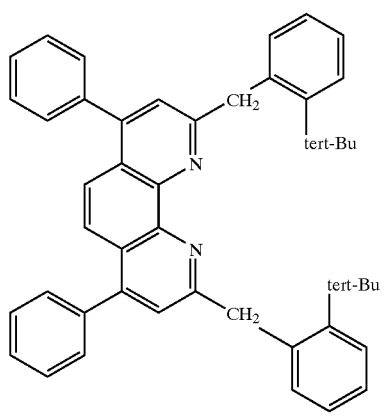
Compound No. 149
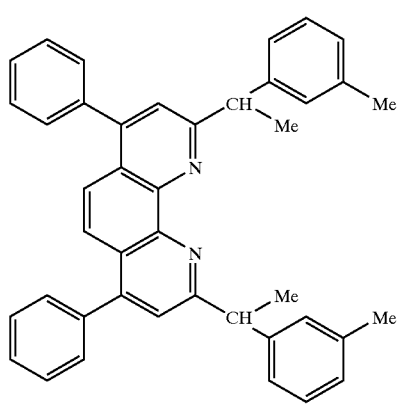

-continued
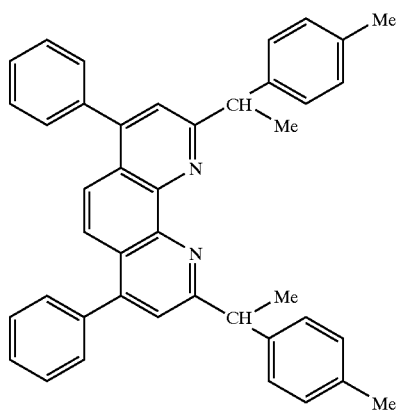
Compound No. 150
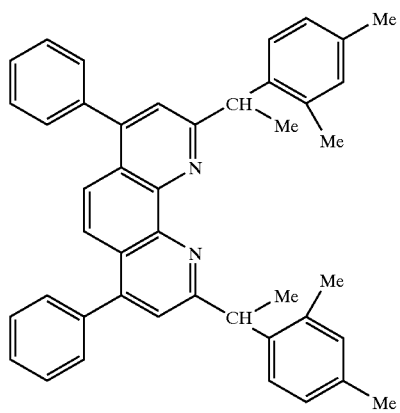
Compound No. 153
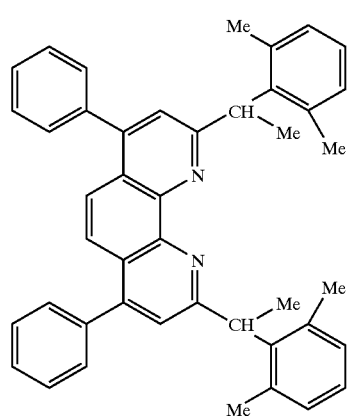
Compound No. 151
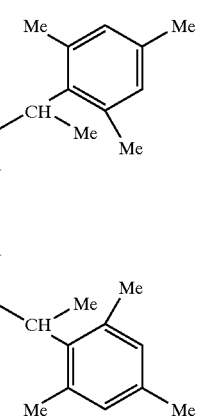
Compound No. 154
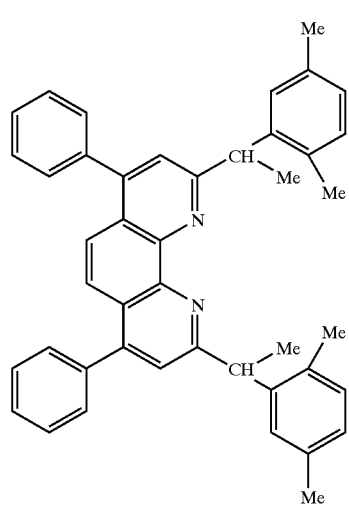
Compound No. 152
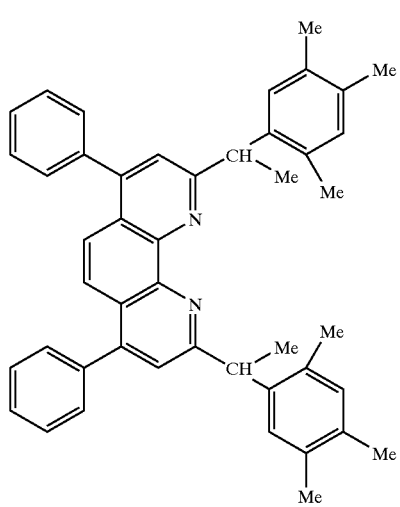
Compound No. 155

-continued
Compound No. 156
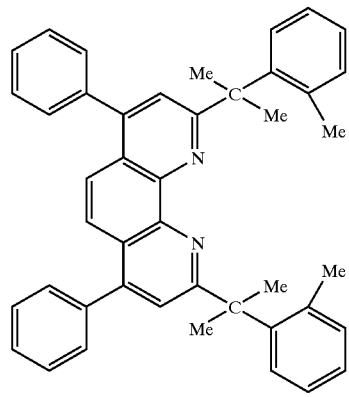
Compound No. 159
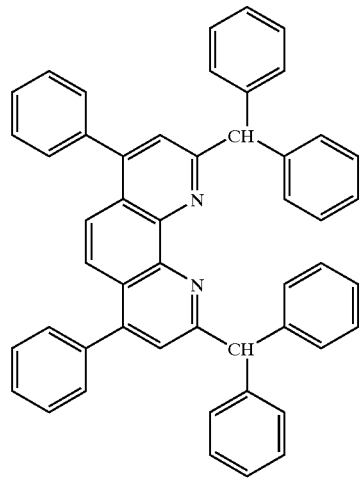
Compound No. 157
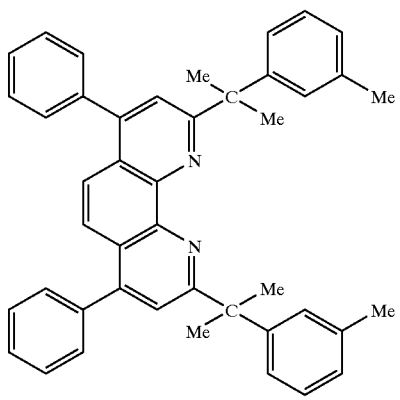
Compound No. 160
Compound No. 158
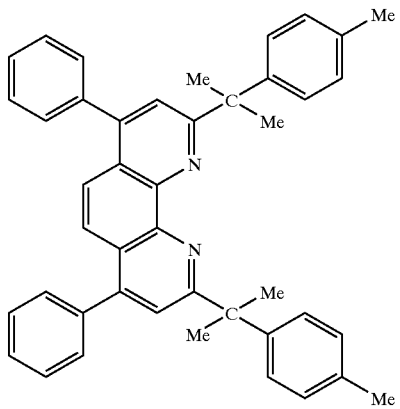
Compound No. 161
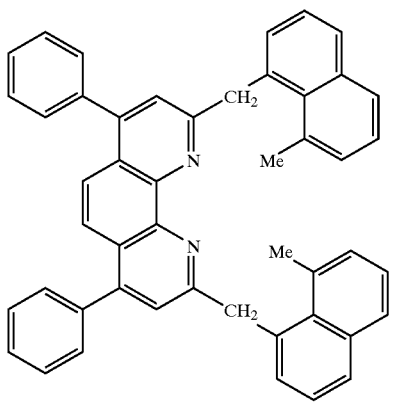

Compound No. 162
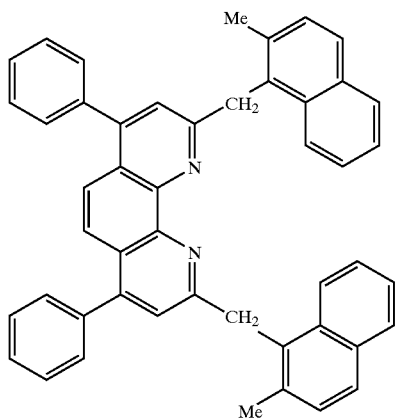
Compound No. 163
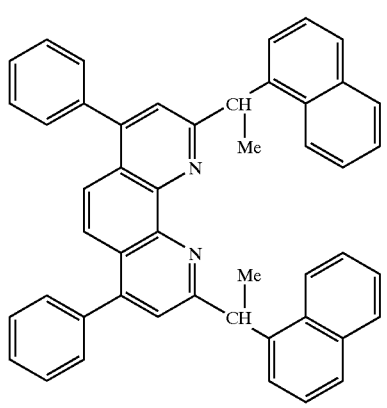
Compound No. 164
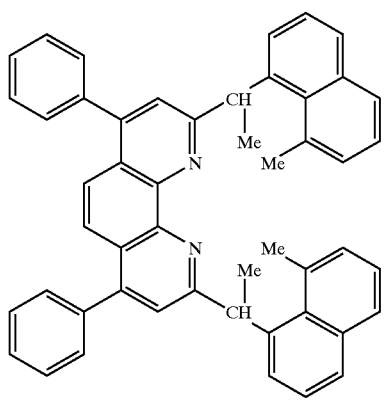
Compound No. 165
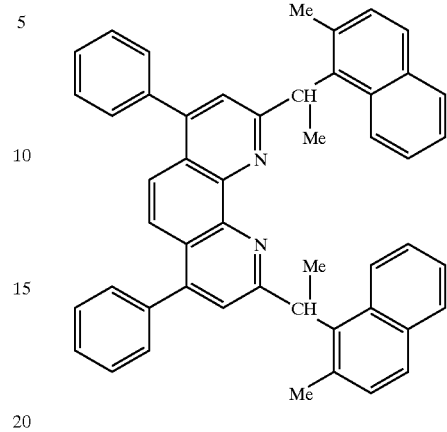
Compound No. 166
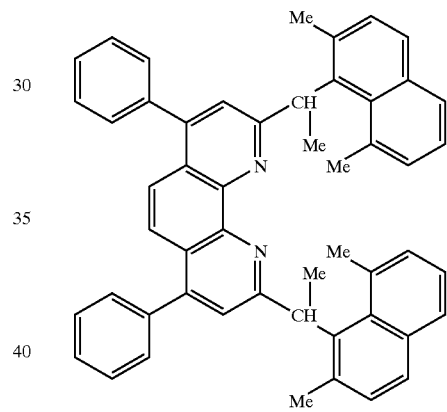
Compound No. 167
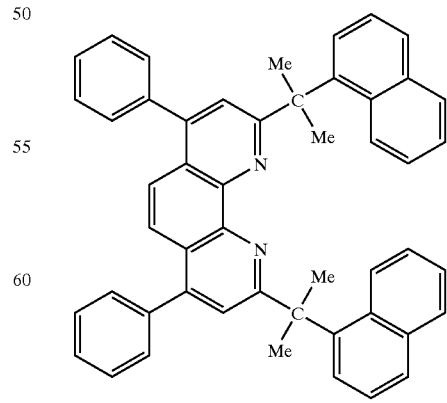

-continued
Compound No. 168
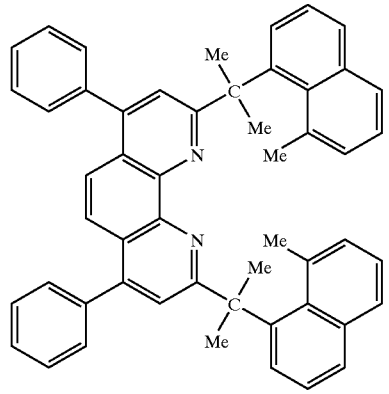
Compound No. 169
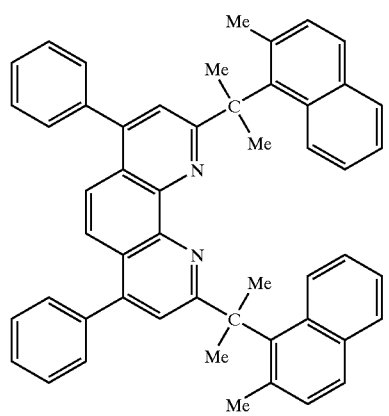
Compound No. 170
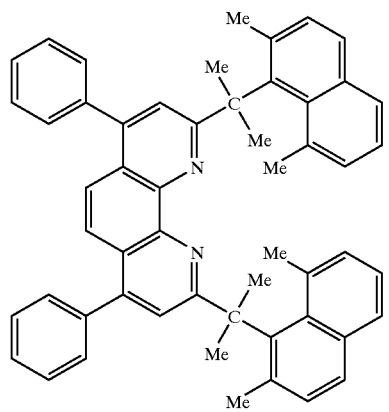
-continued
Compound No. 171
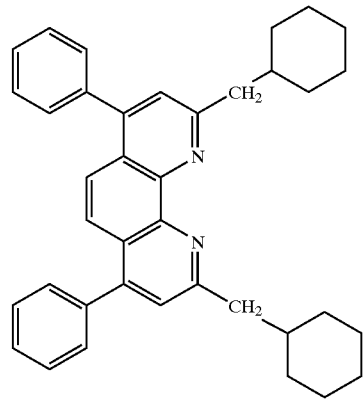
Compound No. 172
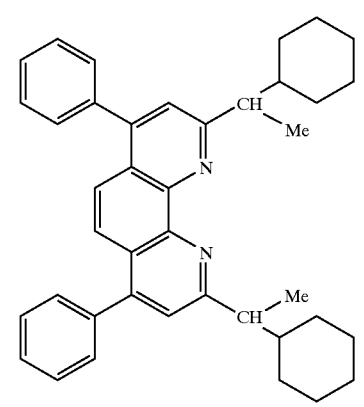
Compound No. 173
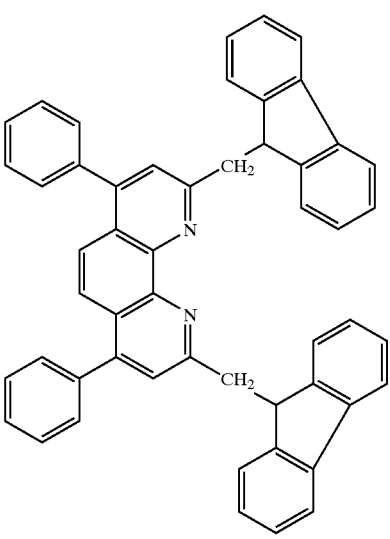

Compound No. 174

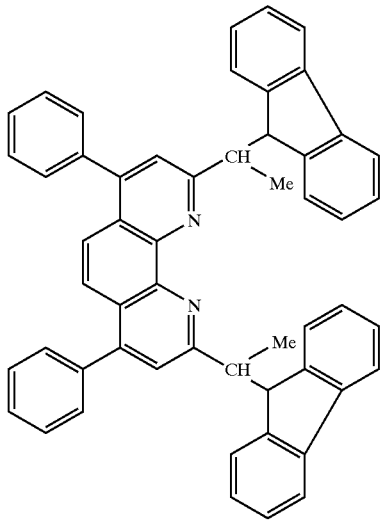

Compound No. 175

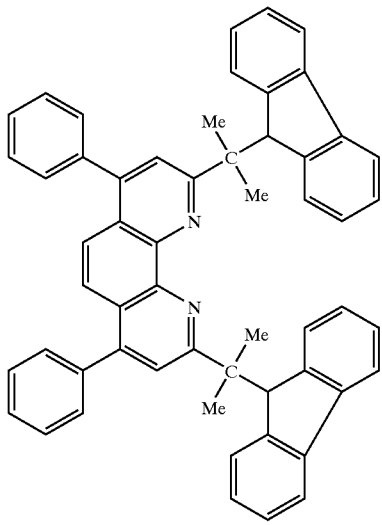

Compound No. 176

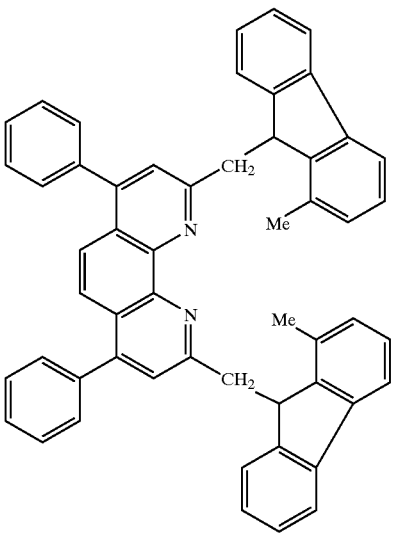

Compound No. 177
Compound No. 178

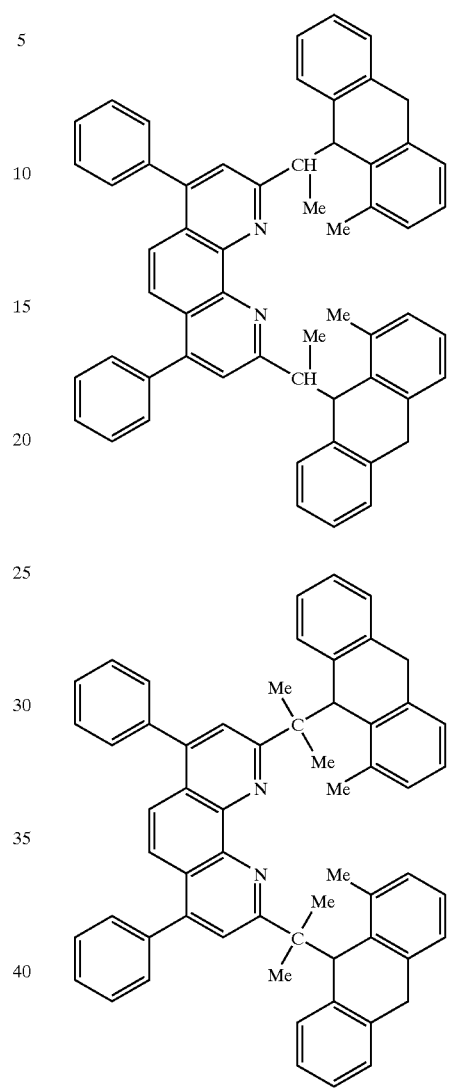

Preferred embodiments of the invention wherein bathophenanthroline compounds of the invention are, respectively, applied to an organic EL device are described.

First Embodiment

FIG. 1 is a schematic sectional view showing an essential part of an organic EL device capable of emitting blue luminescence according to the first embodiment of the invention.

In this embodiment, a transparent electrode, made of ITO (indium tin oxide) or Zn-doped indium oxide, is formed on a glass substrate 6 by sputtering or vacuum deposition, followed by successively forming a hole transporting luminescent layer 4a, a hole transporting luminescent layer 4b, a hole-blocking layer 33 containing a bathophenanthroline (derivative) compound of the afore-indicated general formula, an electron transport layer 2, and a cathode electrode 1 in this order according to a vacuum deposition technique to form an organic EL device (organic EL device) 21 made of the amorphous organic thin films.

This organic EL device 21 has such an arrangement that the hole transport layer 4 serves also as a luminescent layer, and this fundamental structure is likewise employed in other embodiments described hereinafter.

The feature of the organic EL device 21 of this embodiment resides in that the bathophenanthroline derivative-containing layer 33 is interposed, as a hole-blocking layer, between the hole transport layer 4 and the electron transport layer 2, so that the recombination of electrons-holes is promoted in the hole transport layer 4, at which luminescence is emitted, and/or luminescence is also emitted from the bathophenanthroline derivative-containing layer 33.

Figure 2:
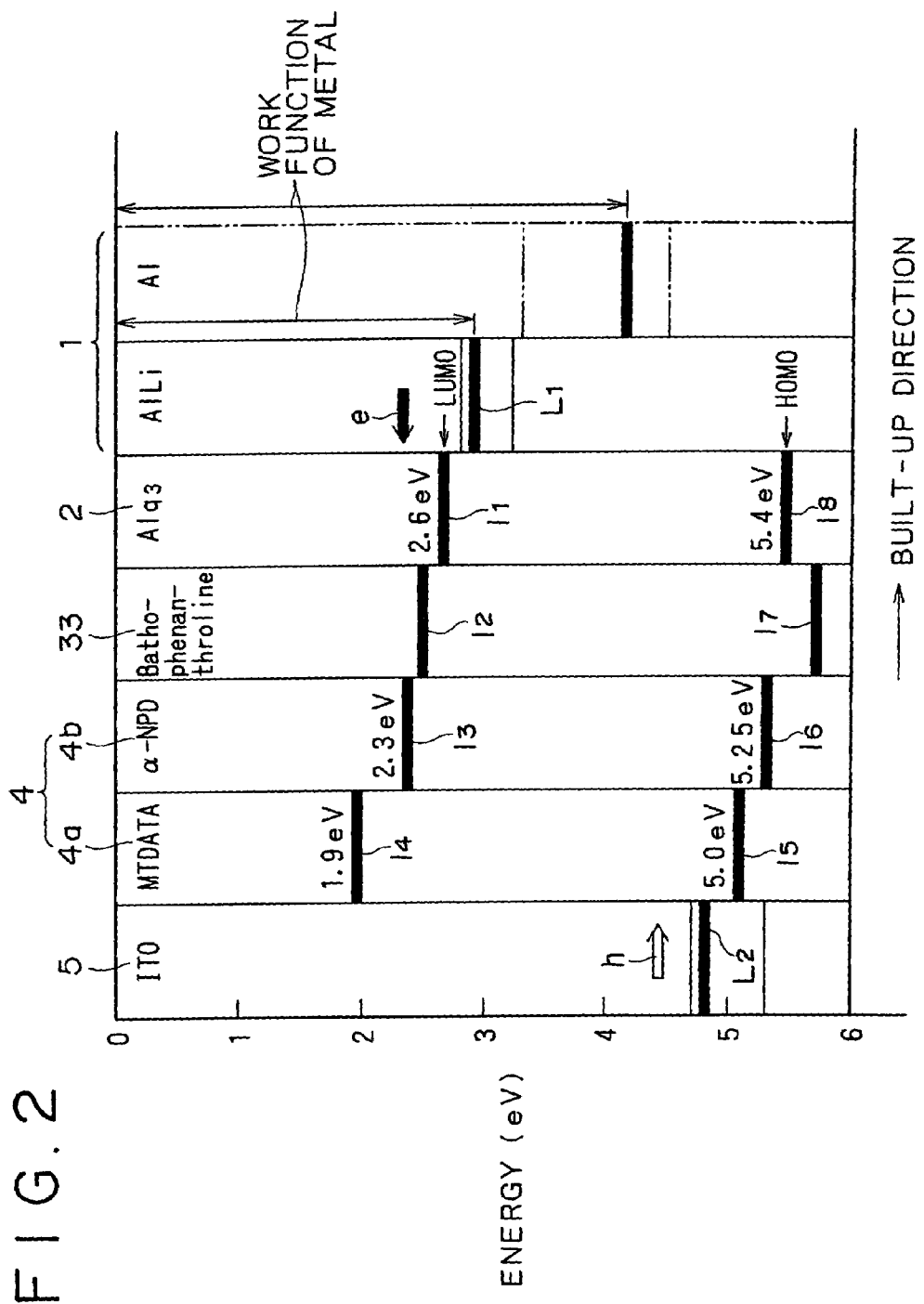
FIG. 2 is a schematic band model view showing a built-up structure of the organic EL device.

FIG. 2 schematically shows the built-up structure of the organic EL device of this embodiment in FIG. 1 as a band model.

In FIG. 2, the thick lines ($L_1$, $L_2$) indicated at the cathode 1 made of Al and Al—Li (aluminium-lithium,) and the ITO transparent electrode 5 layer, respectively, mean approximate work functions of the respective metals. In the respective layers between the electrodes, upper thick lines $l_1$, $l_2$, $l_3$ and $l_4$ and numerical values thereof indicate the lowest unoccupied molecular orbital (LUMO) levels, and lower thick lines $l_5$, $l_6$, $l_7$ and $l_8$ and numerical values thereof indicate the highest occupied molecular orbital (HOMO) levels, respectively. It is to be noted that the energy levels in FIG. 2 are shown only by way of example and may widely vary depending on the types of materials.

In the organic EL device, as shown in FIG. 2, the holes h charged from the transparent electrode 5 serving as an anode are moved via the hole transport layer 4. On the other hand, electrons e charged from the metal electrode 1 serving as a cathode are moved via the electron transport layer 2. The electrons-holes are recombined in the hole transporting luminescent layer, at which luminescence is emitted.

The electrons e charged from the metal electrode 1 serving as a cathode has the tendency of moving toward a lower energy level, and can arrive at the hole transporting luminescent layers 4b, 4a via the lowest unoccupied molecular orbital (LUMO) levels $l_1$ to $l_4$ of the respective layers in the order of the metal electrode 1, electron transport layer 2, hole-blocking layer 33, hole transporting luminescent layer 4b and hole transporting luminescent layer 4a.

On the other hand, the holes h charged from the ITO transparent electrode 5 serving as an anode has the tendency of moving toward a higher energy level, and can move to the electron transport layer 2 via the highest occupied molecular orbital (HOMO) levels 15 to 17 of the respective layers in the order of the hole transporting luminescent layer 4a, hole transporting luminescent layer 4b and hole-blocking layer 33.

However, as shown in FIG. 2, the highest occupied molecular orbital (HOMO) level $l_8$ of the electron transport layer 2 is lower in energy than the highest occupied molecular orbital (HOMO) level $l_7$ of the hole-blocking layer 33. This makes it difficult that the charged holes h moves from the hole-blocking layer 33 toward the electron transport layer 2, and thus, they are filled in the hole-blocking layer 33.

Eventually, the holes h filled in the hole-blocking layer 33 promote the re-combination of electrons-holes at the hole transport layer 4, thereby permitting the luminescent materials of the hole transporting luminescent layers 4a, 4b or the hole transport layer 4 to emit luminescence or light.

In this way, the provision of the hole-blocking layer 33 effectively controls the transport of the holes h in the hole-blocking layer 33 so that the electron-hole re-combination in the hole transport layer 4 is efficiently caused. Thus, light with a specific wavelength (blue) is emitted in the form of light emission mainly from the hole transporting luminescent layer 4b, adjoining to the hole-blocking layer 33, of the light-emitting hole transporting luminescent layers 4a, 4b, to which emission from the hole transporting luminescent layer 4a is added.

Fundamentally, the electron-hole re-combination takes place in the respective layers including the electron transport layer 2 and the hole transport layer 4 as resulting from the charge of electrons from the cathode electrode 1 and the charge of holes from the anode electrode 5. Accordingly, in the absence of such a hole-blocking layer 33 as set out above, the electron-hole re-combination occurs at the interface between the electron transport layer 2 and the hole transport layer 4 so that light emission with a long wavelength alone is obtained. However, when the hole-blocking layer 33 as in this embodiment is provided, it is enabled to promote blue light emission while permitting the luminescent substance-containing hole transport layer 4 as an emission region.

As set out above, the hole-blocking layer 33 is provided to control the transport of the holes h. To this end, it is sufficient that the highest occupied molecular orbital (HOMO) level of the hole-blocking layer 33 is not higher than the HOMO level that is lower in energy between the HOMO levels of the hole transporting luminescent layer 4b and the electron transport layer 2, and that the lowest unoccupied molecular orbital (LUMO) level of the hole-blocking layer 33 is not lower than the LUMO level that is lower in energy and is not higher than the LUMO level that is higher in energy, between the LUMO levels of the hole transporting luminescent layer 4b and the electron transport layer 2. Thus, the invention is not limited to such an arrangement as set out before.

In the practice of the invention, the energy levels may not always be within such ranges as defined before, and the bathophenanthroline compound-containing layer per se may emit light or luminescence. In addition, the hole-blocking layer may be made of a built-up structure including a plurality of layers.

The hole-blocking layer 33 may be formed of the bathophenanthroline derivative and/or other material, and its thickness may be changed within a range permitting its function to be maintained. More particularly, the thickness is preferably within a range of 1 Å to 1,000 Å (0.1 nm to 100 nm). If the thickness is too small, the hole blocking ability becomes incomplete, so that the re-combination region is liable to extend over the hole transport layer and the electron transport layer. On the contrary, when the thickness is too large, light emission may not occur due to the increase in film resistance.

The organic EL device 21 is made by use of a vacuum deposition apparatus 11 shown in FIG. 3. The apparatus 11 has therein a pair of support means 13 fixed below an arm 12. A stage mechanism (not shown) is provided between the fixed support means 13 so that a transparent glass substrate 6 can be turned down and a mask 22 can be set as shown. Below the glass substrate 6 and the mask 22, a shutter 14 supported with a shaft 14a is provided, below which a given number of deposition sources 28 are further provided. The deposition sources are heated by means of a resistance heating system using an electric power supply 29. For the heating, an EB (electron beam) heating system may also be used, if necessary.

In this apparatus, the mask 22 is for pixels, and the shutter 14 is for deposition materials. The shutter 14 is able to rotate about the shaft 14a and has the function of intercepting a deposition stream of a material depending on the sublimation temperature of the deposition material.

Figure 4:
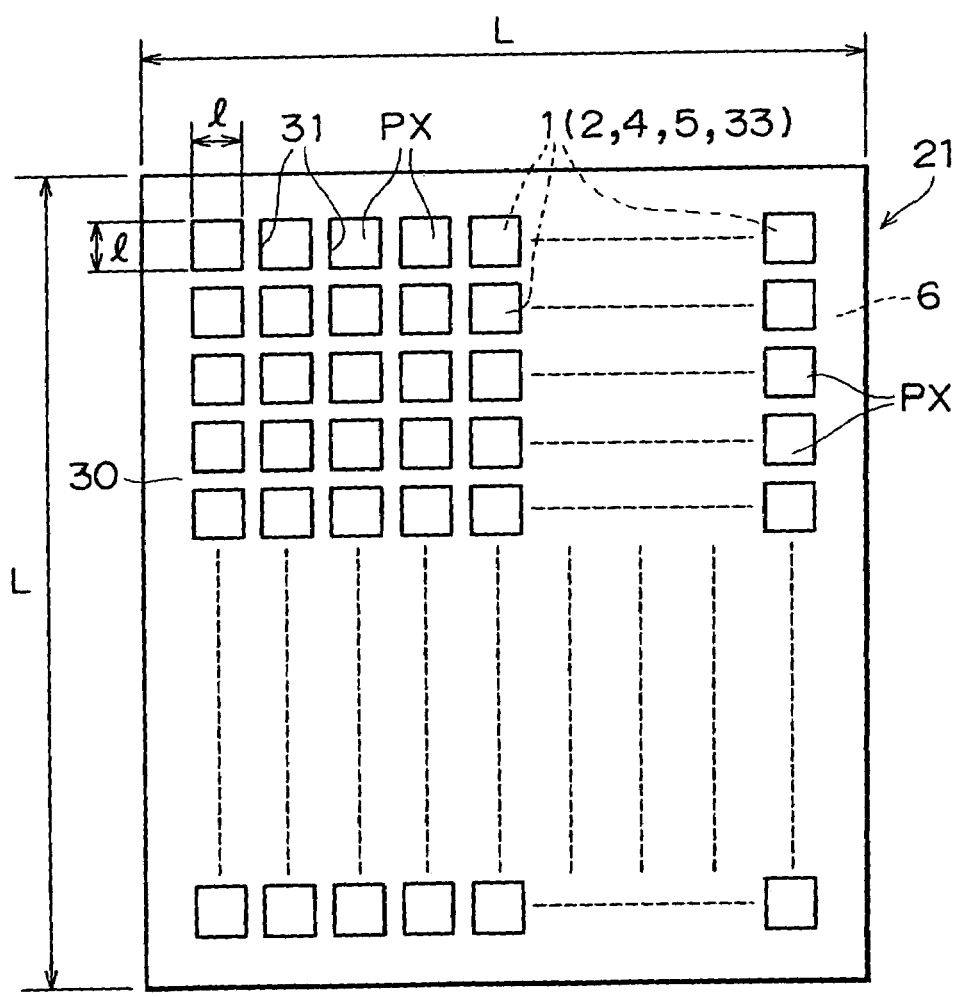
FIG. 4 is a plan view showing the organic EL device.

FIG. 4 is a plan view showing a specific example of the organic EL device fabricated by use of the vacuum deposition apparatus. More particularly, ITO transparent electrodes 5 each with a size of 2 mm×2 mm are vacuum deposited on a glass substrate 6 with a size, L, of 30 mm×30 mm by means of the vacuum deposition apparatus in a thickness of about 100 nm, followed by vacuum deposition of $SiO_2$ 30 over the entire surface thereof and etching in a given pixel pattern to form a multitude of openings 31. In this way, the transparent electrodes 5 are, respectively, exposed. Thereafter, the respective organic layers 4, 33, 2 and a metal electrode 1 are successively formed through a deposition mask 22 of $SiO_2$ on each 2 mm×2 mm emission region (pixel) PX.

Using the vacuum deposition apparatus 11, a large-sized pixel may be singly formed, aside from the device having a multitude of pixels as shown in FIG. 4.

In this way, when the organic layer 33 is formed in order to improve the efficiency of the electron-hole re-combinations in the emission region, there can be obtained an organic EL device that is stable and high in brightness, can be driven at a low voltage and has the hole transporting luminescent layer 4. As will be described in more detail, it is enabled to obtain a brightness of not smaller than 10,000 $cd/m^2$ by DC drive and a peak brightness, calculated as DC, of not smaller than 55,000 $cd/m^2$ by pulse drive at a duty ratio of 1/10 with respect to blue light emission.

The transparent electrode, organic hole transport layer, organic hole-blocking layer, organic electron transport layer and metal electrode of the electroluminescent device may, respectively, have a built-up structure made of a plurality of layers.

The respective organic layers of the electroluminescent device may be formed not only by vacuum deposition, but also other film-forming techniques using sublimation or vaporization, or a technique of spin coating, casting or the like.

The hole transporting luminescent layer of the electroluminescent device may be formed by co-deposition of a small amount of molecules in order to control emission spectra of the device, and may be, for example, an organic thin film containing a small amount of an organic substance such as a perylene derivative, a coumarin derivative or the like.

Usable hole transport materials include, aside from benzidine or its derivatives, styrylamine or its derivatives and triphenylmethane or its derivatives, porphyrin or its derivatives, triazole or its derivatives, imidazole or its derivatives, oxadiazole or its derivatives, polyarylalkanes or derivatives thereof, phenylenediamine or its derivatives, arylamines or derivatives thereof, oxazole or its derivatives, anthracene or its derivatives, fluorenone or its derivatives, hydrazone or its derivatives, stilbene or its derivatives, or heterocyclic conjugated monomers, oligomers, polymers and the like such as polysilane compounds, vinylcarbazole compounds, thiophene compounds, aniline compounds and the like.

More particularly, mention is made of α-naphthylphenyldiamine, porphyrin, metal tetraphenylporphyrins, metal naphthalocyanines, 4,4',4"-trimethyltriphenylamine, 4,4',4"-tris(3-methylphenylphenylamino)triphenylamine, N,N,N',N'-tetrakis(p-tolyl)-p-phenylenediamine, N,N,N',N'-tetraphenyl-4,4'-diaminobiphenyl, N-phenylcarbazole, 4-di-p-tolylaminostilbene, poly(paraphenylenevinylene), poly(thiophenevinylene), poly(2,2'-thienylpyrrole) and the like, although not limited thereto.

Usable electron transport materials include quinoline or its derivatives, perylene or its derivatives, bistylyl or its derivatives, pyrazine or its derivatives, and the like.

More specifically, mention is made, for example, of 8-hydroxyquinoline aluminium, anthracene, naphthalene, phenanthrene, pyrene, chrysene, perylene, butadiene, coumarin, acridine, stilbene, or derivatives thereof.

The materials used as the anode electrode or cathode electrode of the electroluminescent device are not limitative in types.

The cathode electrode material should preferably be made of a metal whose work function from a vacuum level of an electrode material is small in order to efficiently charge electrons. There may be used, aside from an aluminium-lithium alloy, low work function metals such as, for example, aluminium, indium, magnesium, silver, calcium, barium, lithium and the like, singly or in the form of alloys with other metals for enhancing the stability thereof.

In order to take out organic electroluminescence from the side of the anode electrode, ITO is used as a transparent anode electrode in examples appearing hereinafter. Nevertheless, there may be used electrode materials, which have a great work function from the vacuum level of an anode electrode material and include, for example, gold, a stannic oxide-antimony mixture, a zinc oxide-aluminium mixture or the like, so as to efficiently charge holes.

The substrate 2 may not be limited to a glass substrate, but may be made of an opaque material. More particularly, there may be used, for example, a silicon substrate, a Cr substrate, or a substrate made of glass, on which a metal is formed by vacuum deposition. Where a substrate made of an opaque material is used, it is preferred that the upper surface of an organic EL device (i.e. the side of the cathode electrode) is formed of a transparent or translucent material so that electroluminescence is picked out to outside. ITO may be used for this purpose, for example.

There can be made an organic EL device for full color or multi-color, which is capable of emission of primaries of R, G and B, by proper choice of luminescent materials, not to mention an organic EL device for monochrome. Besides, the organic EL device of the invention is usable not only for display, but also for light source along with its application to other optical use.

It will be noted that the organic EL device may be sealed with germanium oxide or the like so as to enhance the stability thereof by suppressing the influence of oxygen or the like in air, or may be driven under conditions drawn to vacuum.

Second Embodiment

Figure 5:
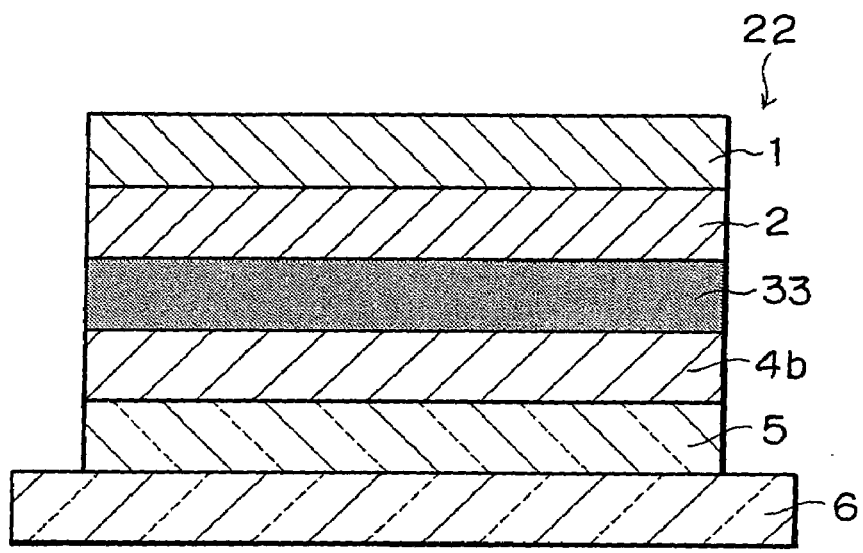
FIG. 5 is a schematic sectional view showing an essential part of another type of organic EL device using a bathophenanthroline compound of the invention.

FIG. 5 is a schematic sectional view showing an essential part of an organic EL device according to a second embodiment of the invention. An organic EL device 22 of this embodiment differs from that of FIG. 1 in that the hole transporting luminescent layer 4b is formed on the ITO transparent electrode 5 so that the hole transporting luminescent layer is formed as a single layer.

Third Embodiment

Figure 6:
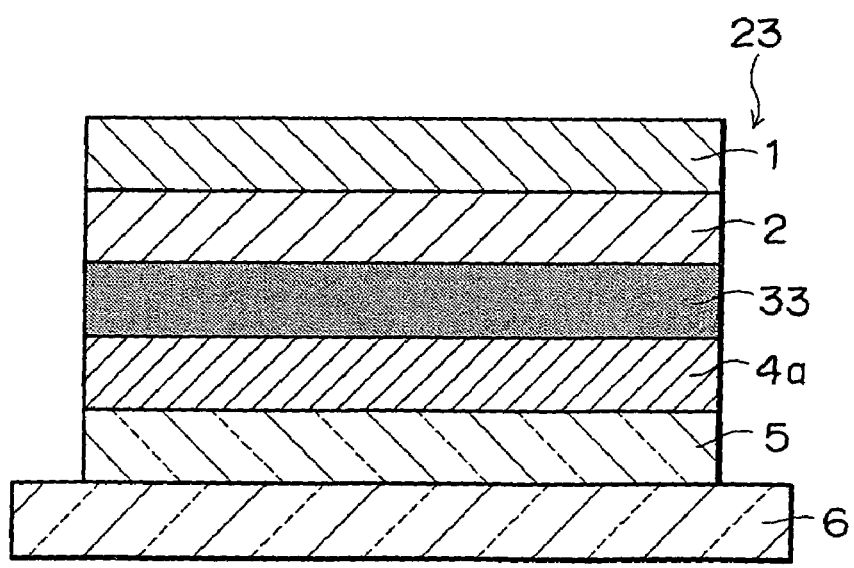
FIG. 6 is a schematic sectional view showing an essential part of further another type of organic EL device using a bathophenanthroline compound of the invention.
Figure 7:
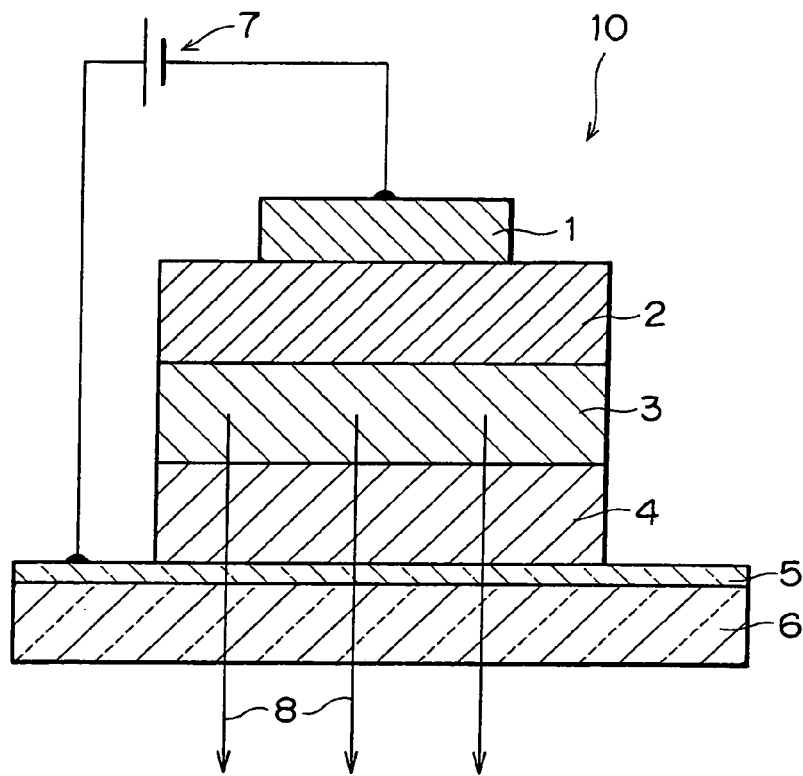
FIG. 7 is a schematic sectional view showing an example of a prior-art organic EL device.
Figure 8:
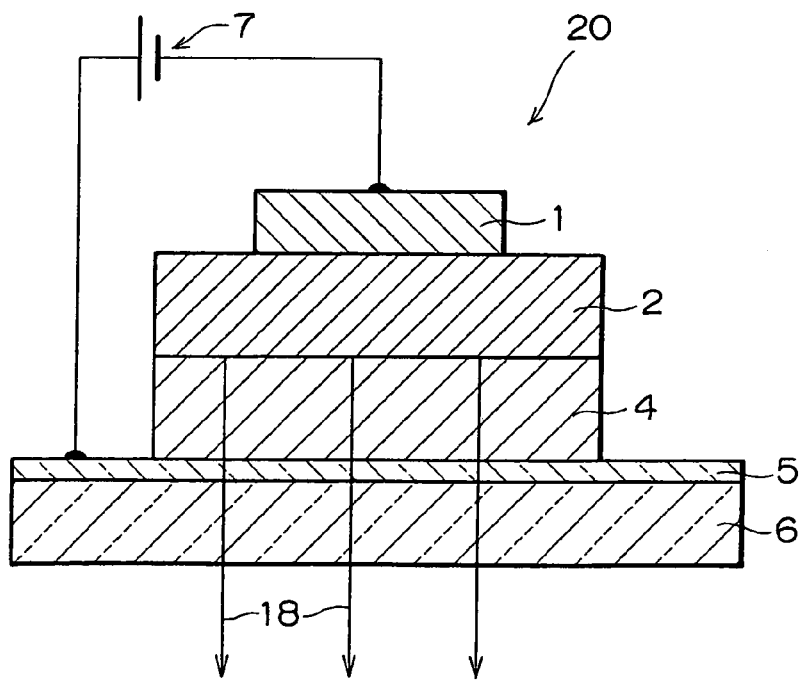
FIG. 8 is a schematic sectional view showing an example of another type of prior-art organic EL device.

FIG. 6 is a schematic sectional view showing an essential part of an organic EL device according to a third embodiment of the invention.

An organic EL device 23 of this embodiment differs from that of FIG. 1 in that a hole transport layer (serving also as a hole transporting luminescent layer) 4a is formed on the ITO transparent electrode 5, and thus, the hole transporting luminescent layer is formed as a single layer, like the second embodiment.

The invention is more particularly described by way of examples.

EXAMPLE 1

Preparation of 2,9-di(2-methylphenyl)bathophenanthroline
The reaction sequence is shown below n-Butyl lithium (1.6 M n-hexane solution, 17.0 ml, 26.8 mmol) was gradually dropped in an n-hexane solution (40 ml) of 2-iodotoluene (5.84 g, 26.4 mmol) at room temperature. After completion of the dropping, the reaction solution was agitated at room temperature for 16 hours, and the resultant product was separated by filtration, followed by washing of the resulting white solid with n-hexane (40 ml×3 times). A toluene solution (50 ml) of bathophenanthroline (2.03 g, 6.11 mmol) was gradually dropped, at room temperature, in an anhydrous diethyl ether/toluene (3:1) solution (20 ml) of the resulting white solid, followed by agitation at room temperature for 16 hours.

60 ml of iced water was added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=4:1→2:1), followed by recrystallization (solvent for recrystallization: chloroform/n-hexane=2:1) to obtain the intended compound (1.01 g, yield: 49.5%) as light yellow crystals.

The product was identified through $^1$H-NMR (solvent: chloroform) and FAB-MS measurements.

$^1$H-NMR: 2.70 (m, 6H, CH$_3$—Ar—), 7.25–7.75 (s, 18H, aromatic), 7.80 (s, 2H, aromatic), 7.90 (s, 2H, aromatic)

MS: m/s (relative intensity) 512 (M$^+$, 100)

The visible light absorption maximum wavelength of a tetrahydrofuran (THF) solution of the product was at 297 nm, with a fluorescent wavelength being at 390 nm.

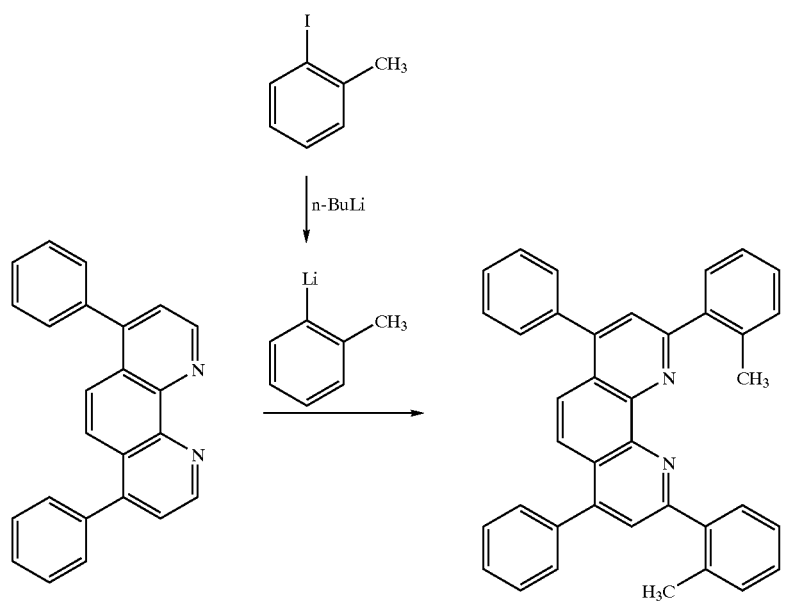

EXAMPLE 2

Preparation of 2,9-di(2,6-dimethylphenyl)-bathophenanthroline

The reaction sequence is shown below

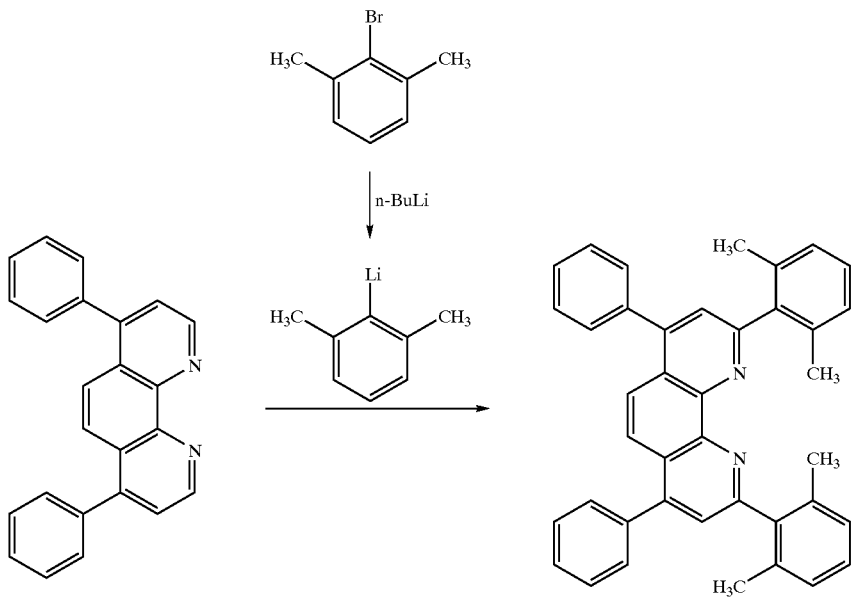

n-Butyl lithium (1.6 M n-hexane solution, 60.2 ml, 96.3 mmol) was gradually dropped in an n-hexane/anhydrous diethyl ether (10:1) solution (110 ml) of 2-bromo-m-xylene (17.8 g, 96.3 mmol) at room temperature. After completion of the dropping, the reaction solution was heated under reflux for 2 hours and further agitated at room temperature for 16 hours, and the resultant product was separated by filtration, followed by washing of the resulting white solids with n-hexane (50 ml×3 times). A toluene solution (80 ml) of bathophenanthroline (5.09 g, 15.3 mmol) was gradually dropped, at room temperature, in an anhydrous diethyl ether solution (40 ml) of the resulting white solids. After completion of the dropping, the solution was heated under reflux for 2 hours and agitated at room temperature for 16 hours.

60 ml of iced water was gradually added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=8:1→4:1), followed by recrystallization (solvent for recrystallization: chloroform/n-hexane=2:1) to obtain the intended compound (2.00 g, yield: 39.4%) as light yellow crystals.

The product was identified through $^1$H-NMR and FAB-MS measurements.

$^1$H-NMR: 2.25 (m, 12H, CH$_3$—Ar—), 7.05–7.25 (s, 6H, aromatic), 7.35–7.70 (s, 12H, aromatic), 7.95 (s, 2H, aromatic)

MS: m/s (relative intensity) 540 (M$^+$, 100)

The visible light absorption maximum wavelength of a THF solution of the product was at 286 nm, with a fluorescent wavelength being at 380 nm.

EXAMPLE 3

Preparation of 2,9-dinaphthyl-bathophenanthroline

The reaction sequence is shown below

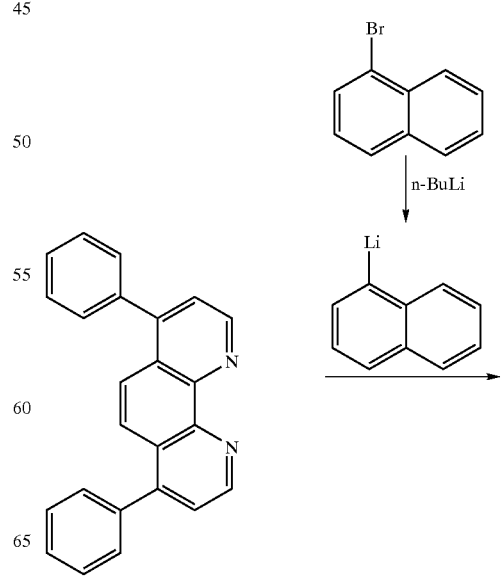

-continued

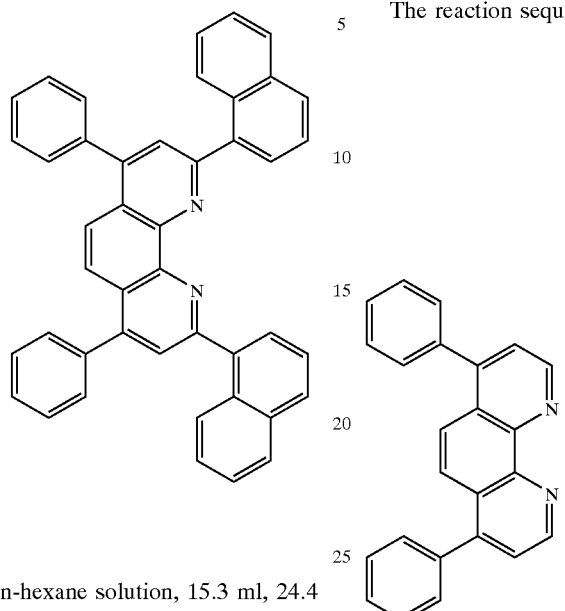

n-Butyl lithium (1.6 M n-hexane solution, 15.3 ml, 24.4 mmol) was gradually dropped, at 0° C., in an n-hexane/anhydrous diethyl ether (1:1) solution (60 ml) of 1-bromonaphthalene (5.01 g, 24.4 mmol). After completion of the dropping, the reaction solution was agitated at room temperature for 16 hours, and the resultant product was subsequently separated by filtration, and the residue was washed with n-hexane (40 ml×3 times). A toluene solution (80 ml) of bathophenanthroline (2.03 g, 6.11 mmol) was gradually dropped, at room temperature, in an anhydrous diethyl ether solution (40 ml) of the resulting solids. After completion of the dropping, the reaction solution was agitated at room temperature for 16 hours.

60 ml of iced water was gradually added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=8:1→4:1), followed by recrystallization (solvent for recrystallization: chloroform/n-hexane=2:1) to obtain the intended compound (1.38 g, yield: 68.2%).

The product was identified through $^1$H-NMR and FAB-MS measurements.

$^1$H-NMR: 7.30–8.00 (s, 24H, aromatic), 8.32 (s, 2H, aromatic), 8.68 (s, 2H, aromatic)

MS: m/s (relative intensity) 584 (M$^+$, 100)

EXAMPLE 4

Preparation of 2,9-difluorenyl-bathophenanthroline
The reaction sequence is shown below

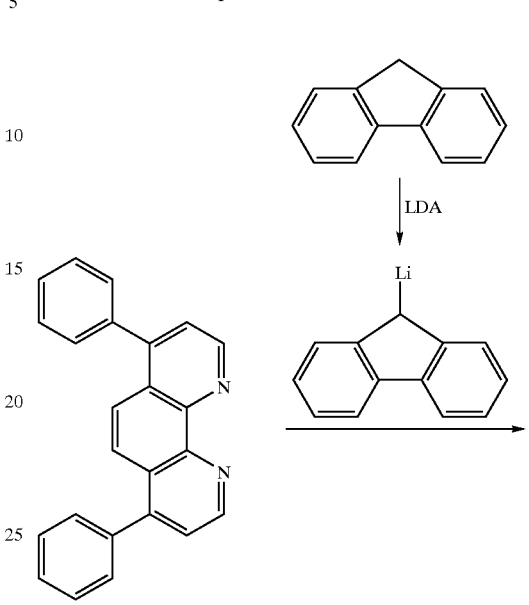

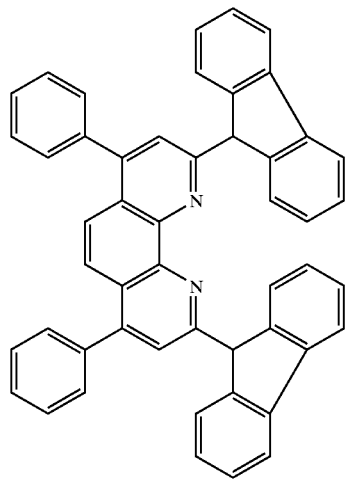

Lithium diisopropylamine (LDA) (1.89 g, 17.4 mmol) was added to a THF solution (30 ml) of fluorene (4.16 g, 25.0 mmol) and agitated at room temperature for 16 hours. Thereafter, the THF and diisopropylamine were removed by distillation under reduced pressure. A toluene solution (60 ml) of bathophenanthroline (2.03 g, 6.11 mmol) was gradually dropped in an anhydrous diethyl ether solution (20 ml) of the resultant yellow solids at room temperature. After the dropping, the reaction solution was heated under reflux for 2 hours and agitated at room temperature for 16 hours.

60 ml of iced water was gradually added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=8:1→4:1), followed by recrystallization (solvent for recrystallization: chloroform/n-hexane=2:1) to obtain the intended compound (1.38 g, yield: 68.2%).

The product was identified through ¹H-NMR and FAB-MS measurements.

¹H-NMR: 4.51 (m, 2H, Ar—CH$_2$—Ar), 7.30–7.78 (s, 28H, aromatic), 7.81 (s, 2H, aromatic)

MS: m/s (relative intensity) 660 (M⁺, 100)

EXAMPLE 5

Preparation of 2,9-dibenzyl-bathophenanthroline
The reaction sequence is shown below

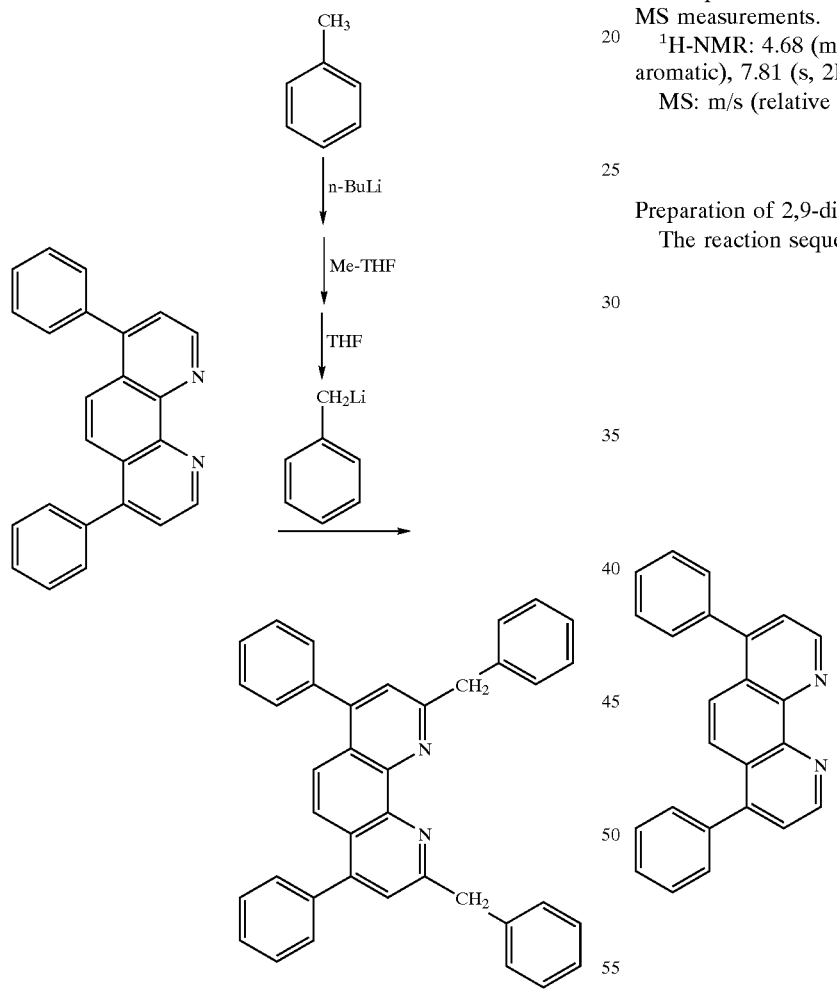

n-Butyl lithium (1.6 M n-hexane solution, 4.45 ml, 7.13 mmol) was gradually dropped in anhydrous toluene (2.24 g, 24.9 mmol) at room temperature. After completion of the dropping, Me-THF (0.627 g, 7.47 mmol) was further added to the solution at −22° C. in 20 minutes. Thereafter, THF (1.06 g, 14.7 mmol) was added to in 30 minutes, followed by agitation at 6 to 10° C. for 16 hours. A toluene solution (40 ml) of bathophenanthroline (2.03 g, 6.11 mmol) was gradually dropped, at room temperature, in the resultant reaction solution. After completion of the dropping, the reaction solution was agitated at room temperature for 16 hours.

60 ml of iced water was gradually added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=8:1→4:1), followed by recrystallization (solvent for recrystallization: chloroform/n-hexane=2:1) to obtain the intended compound (0.88 g, yield: 43.3%).

The product was identified through ¹H-NMR and FAB-MS measurements.

¹H-NMR: 4.68 (m, 4H, —CH$_2$—Ar), 7.28–7.78 (s, 22H, aromatic), 7.81 (s, 2H, aromatic)

MS: m/s (relative intensity) 512 (M⁺, 100)

EXAMPLE 6

Preparation of 2,9-dicyclohexyl-bathophenanthroline
The reaction sequence is shown below

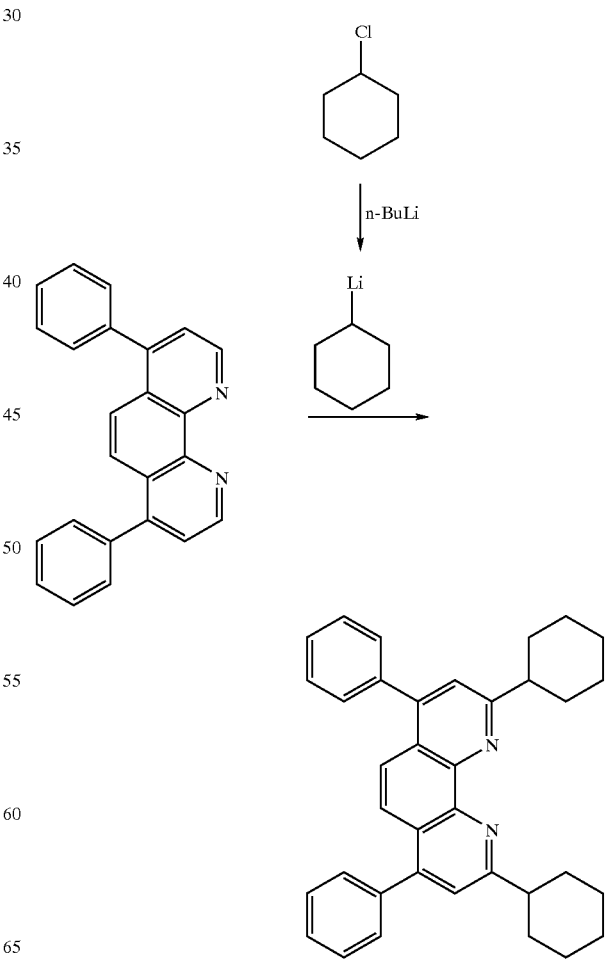

n-Butyl lithium (1.6 M n-hexane solution, 36.3 ml, 58.0 mmol) was gradually dropped, at room temperature, in an n-hexane/anhydrous diethyl ether (10:1) solution (50 ml) of chlorocyclohexane (3.00 g, 25.0 mmol). After completion of the dropping, the reaction solution was further agitated at room temperature for 16 hours, and the resultant product was subsequently separated by filtration, and the resulting white solids were washed with n-hexane (50 ml×3 times). A toluene solution (40 ml) of bathophenanthroline (2.03 g, 6.11 mmol) was gradually dropped, at room temperature, in an anhydrous diethyl ether solution (10 ml) of the resulting white solids. After completion of the dropping, the reaction solution was agitated at room temperature for 16 hours.

60 ml of iced water was gradually added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=8:1→4:1), followed by recrystallization (solvent for recrystallization: chloroform/n-hexane=2:1) to obtain the intended compound (0.98 g, yield: 48.3%).

The product was identified through $^1$H-NMR and FAB-MS measurements.

$^1$H-NMR: 0.80–2.45 (m, 20H, —CH$_2$—CH$_2$—CH$_2$—CH$_2$—CH$_2$—), 3.20 (m, 2H, —CH—Ar), 7.25–7.75 (S, 12H, aromatic), 7.81 (s, 2H, aromatic)

MS: m/s (relative intensity) 496 (M$^+$, 100)

EXAMPLE 7

Preparation of 2,9-dibiphenyl-bathophenanthroline
The reaction sequence is shown below

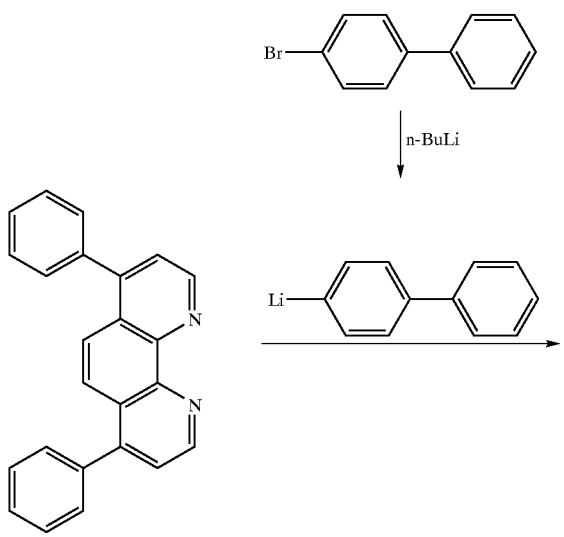

-continued

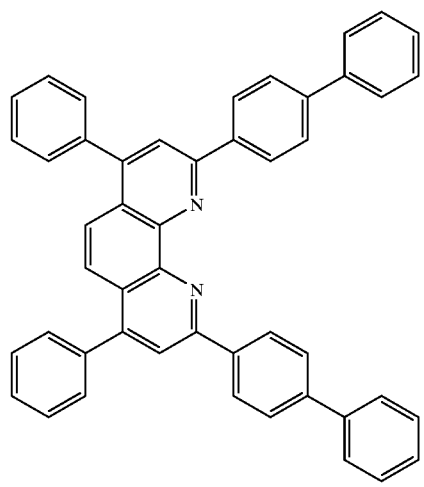

n-Butyl lithium (1.6 M n-hexane solution, 17.0 ml, 27.2 mmol) was gradually dropped, at room temperature, in an n-hexane/anhydrous diethyl ether (10:1) solution (110 ml) of 4-boromobiphenyl (6.33 g, 27.2 mmol). After completion of the dropping, the reaction solution was agitated at room temperature for 16 hours, and the resultant product was subsequently separated by filtration, and the resulting white solids were washed with n-hexane (50 ml×3 times). A toluene solution (40 ml) of bathophenanthroline (2.03 g, 6.11 mmol) was gradually dropped, at room temperature, in an anhydrous diethyl ether solution (20 ml) of the resulting white solids. After completion of the dropping, the reaction solution was agitated at room temperature for 16 hours.

60 ml of iced water was gradually added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=8:1→4:1), followed by recrystallization (solvent for recrystallization: chloroform/n-hexane=2:1) to obtain the intended compound (0.76 g, yield: 3.7.4%).

The product was identified through $^1$H-NMR and FAB-MS measurements.

$^1$H-NMR: 7.25–7.78 (s, 26H, aromatic), 7.81 (s, 2H, aromatic), 8.32 (s, 4H, aromatic)

MS: m/s (relative intensity) 636 (M$^+$, 100)

EXAMPLE 8

Preparation of 2,9-di(2-methylbenzyl)-bathophenanthroline
The reaction sequence is shown below

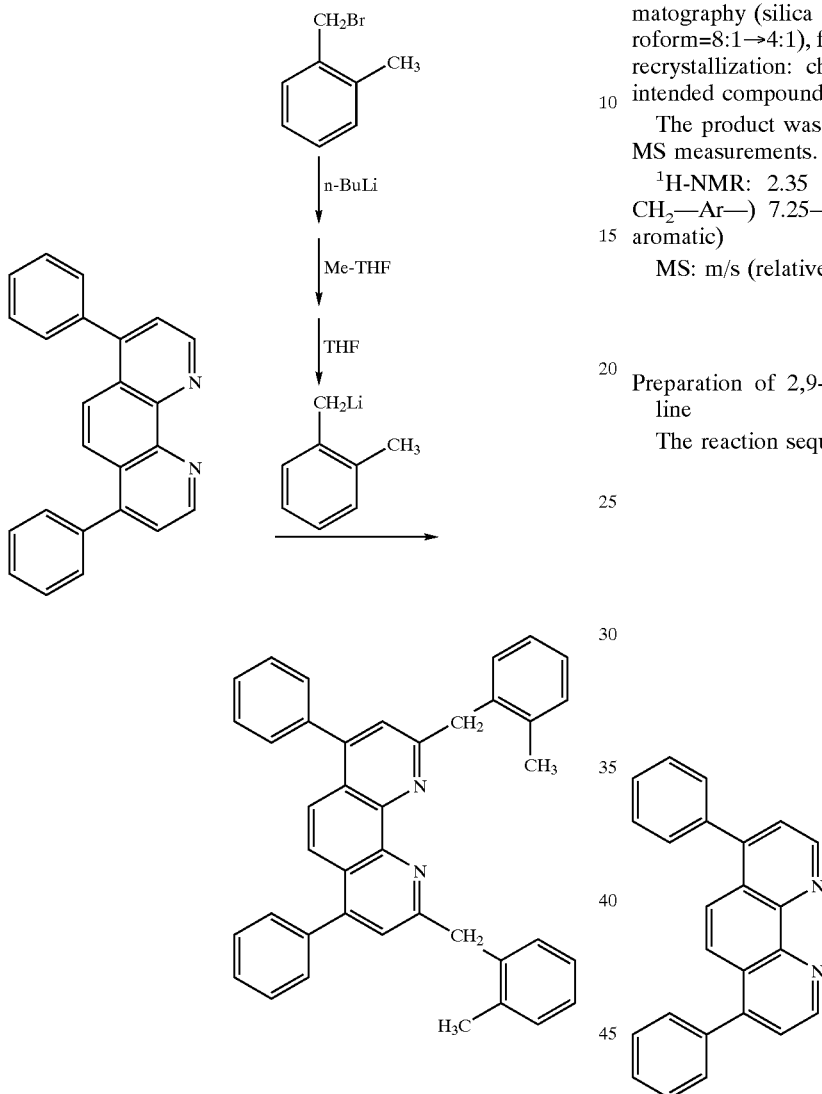

n-Butyl lithium (1.6 M n-hexane solution, 4.45 ml, 7.13 mmol) was gradually dropped in α-bromo-o-xylene (4.91 g, 24.9 mmol) at room temperature. After completion of the dropping, Me-THF (0.627 g, 7.47 mmol) was added in 20 minutes at −22° C., after which THF (1.06 g, 14.7 mmol) was further added in 30 minutes, followed by further agitation at 6 to 10° C. for 16 hours. A toluene solution (40 ml) of bathophenanthroline (2.03 g, 6.11 mmol) was gradually dropped in the resultant reaction solution at room temperature. After completion of the dropping, the reaction solution was agitated at room temperature for 16 hours.

60 ml of iced water was gradually added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=8:1→4:1), followed by recrystallization (solvent for recrystallization: chloroform/n-hexane=2:1) to obtain the intended compound (0.72 g, yield: 35.4%).

The product was identified through $^1$H-NMR and FAB-MS measurements.

$^1$H-NMR: 2.35 (m, 6H, CH$_3$—Ar—), 4.65 (m, 4H, CH$_2$—Ar—) 7.25–7.78 (s, 20H, aromatic), 7.81 (s, 2H, aromatic)

MS: m/s (relative intensity) 540 (M$^+$, 100)

EXAMPLE 9

Preparation of 2,9-di(8-methylnaphthyl)-bathophenanthroline
The reaction sequence is shown below

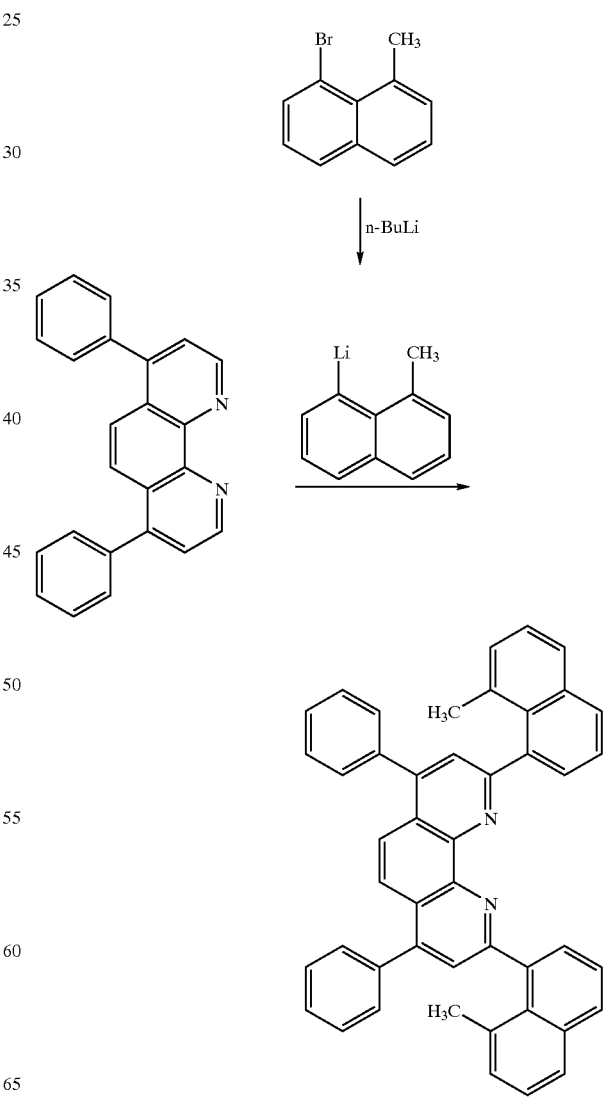

n-Butyl lithium (1.6 M n-hexane solution, 15.3 ml, 24.4 mmol) was gradually dropped, at 0° C., in an n-hexane/anhydrous diethyl ether (1:1) solution (60+ml) of 1-bromo-8-methylnaphthalene (5.34 g, 24.4 mmol). After completion of the dropping, the reaction solution was agitated at room temperature for 16 hours, and the resultant product was subsequently separated by filtration, and the residue was washed with n-hexane (40 ml×3 times). A toluene solution (80 ml) of bathophenanthroline (2.03 g, 6.11 mmol) was gradually dropped, at room temperature, in an anhydrous diethyl ether solution (40 ml) of the resulting solids. After completion of the dropping, the reaction solution was agitated at room temperature for 16 hours.

60 ml of iced water was gradually added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=8:1→4:1), followed by recrystallization (solvent for recrystallization: chloroform/n-hexane=2:1) to obtain the intended compound (1.30 g, yield: 64.0%).

The product was identified through $^1$H-NMR and FAB-MS measurements.

$^1$H-NMR: 2.60 (m, 6H, CH$_3$—Ar—), 7.30–7.81 (s, 22H, aromatic), 7.81 (s, 2H, aromatic), 8.25 (s, 2H, aromatic)

MS: m/s (relative intensity) 612 (M$^+$, 100)

EXAMPLE 10

Preparation of 2,9-di(2-methylnaphthyl)-bathophenanthroline

The reaction sequence is shown below

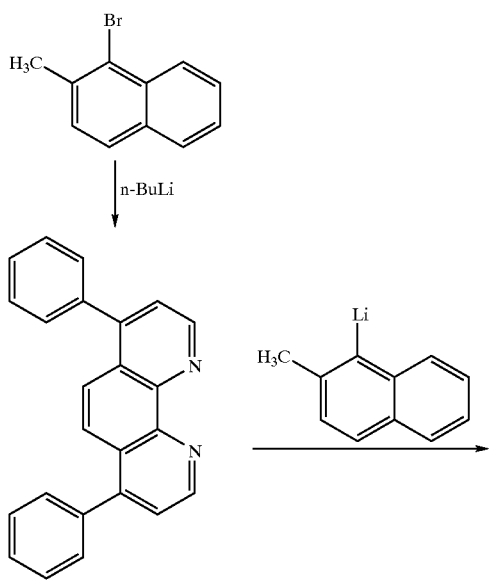

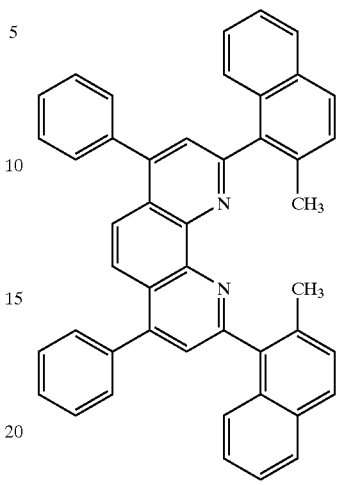

n-Butyl lithium (1.6 M n-hexane solution, 15.3 ml, 24.4 mmol) was gradually dropped, at 0° C., in an n-hexane/anhydrous diethyl ether (1:1) solution (60 ml) of 1-boromo-2-methylnaphthalene (5.34 g, 24.4 mmol). After completion of the dropping, the reaction solution was agitated at room temperature for 16 hours, and the resultant product was subsequently separated by filtration, and the residue was washed with n-hexane (40 ml×3 times). A toluene solution (80 ml) of bathophenanthroline (2.03 g, 6.11 mmol) was gradually dropped, at room temperature, in an anhydrous diethyl ether solution (40 ml) of the resulting solids. After completion of the dropping, the reaction solution was agitated at room temperature for 16 hours.

60 ml of iced water was gradually added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=8:1→4:1), followed by recrystallization (solvent for recrystallization: chloroform/n-hexane=2:1) to obtain the intended compound (1.20 g, yield: 59.1%).

The product was identified through $^1$H-NMR and FAB-MS measurements.

$^1$H-NMR: 2.80 (m, 6H, CH$_3$—Ar—), 7.25–7.78 (s, 24H, aromatic), 7.81 (s, 2H, aromatic)

MS: m/s (relative intensity) 612 (M$^+$, 100)

EXAMPLE 11

Preparation of 2,9-di(α-methylbenzyl)-bathophenanthroline
The reaction sequence is shown below

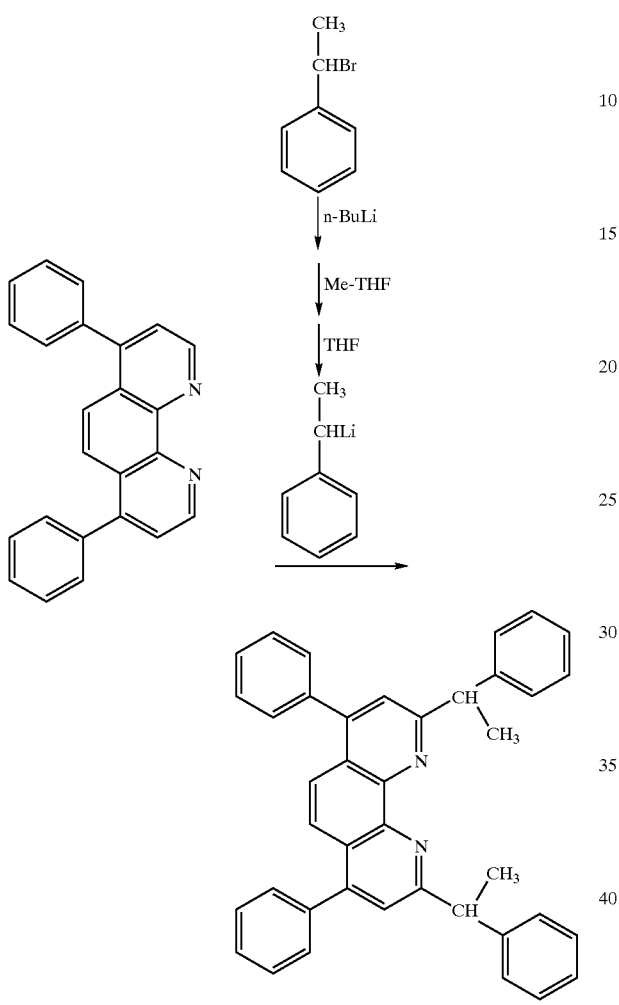

n-Butyl lithium (1.6 M n-hexane solution, 4.45 ml, 7.13 mmol) was gradually dropped in 1-bromo-1-phenylethane (4.91 g, 24.9 mmol) at room temperature. After completion of the dropping, Me-THF (0.627 g, 7.47 mmol) was added in 20 minutes at −22° C., after which THF (1.06 g, 14.7 mmol) was further added in 30 minutes, followed by further agitation at 6 to 1° C. for 16 hours. A toluene solution (40 ml) of bathophenanthroline (2.03 g, 6.11 mmol) was gradually dropped in the resultant reaction solution at room temperature. After completion of the dropping, the reaction solution was agitated at room temperature for 16 hours.

60 ml of iced water was gradually added to the resultant reaction solution to separate an organic layer therefrom. The aqueous layer was extracted three times with chloroform, and the resultant organic layer was mixed with the previously separated organic layer. 60 g of manganese dioxide (chemically treated product) was added to the thus mixed organic layer and agitated for 30 minutes, after which 100 g of sodium sulfate was further added, followed by agitation for 30 minutes.

The resulting mixed solution was filtered and concentrated, and the residue was purified through column chromatography (silica gel, developing solvent: n-hexane/chloroform=8:1→4:1), followed by recrystallization (solvent for recrystallization: chloroform/n-hexane=2:1) to obtain the intended compound (0.83 g, yield: 40.9%).

The product was identified through $^1$H-NMR and FAB-MS measurements.

$^1$H-NMR: 2.40 (m, 6H, CH$_3$—Ar—), 4.64 (m, 2H, —CH—Ar—), 7.25–7.78 (s, 22H, aromatic), 7.81 (s, 2H, aromatic)

MS: m/s (relative intensity) 540 (M$^+$, 100)

As will be appreciated from the foregoing, the bathophenanthroline compounds of the invention can control, for example, carrier transportability depending on the type of substituent to be introduced into the molecule, thus permitting one to utilize them as a carrier transport material of various types of organic EL devices. Moreover, these compounds have high glass transition point and melting point and are thus stable electrically, thermally and/or chemically. In addition, the compounds are sublimable in nature, thus leading to the advantage that they are be readily formed as a uniform amorphous film according to a vacuum deposition process. The bathophenanthroline compound of the invention can be efficiently prepared through nucleophilic substitution reaction using an organolithium compound.

What is claimed is:

1. A bathophenanthroline compound of formula (I):

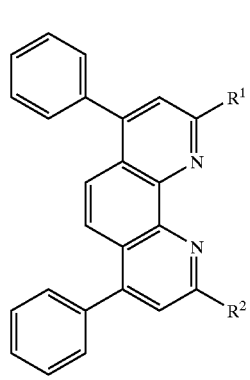

wherein R$^1$ and R$^2$ are selected from the group consisting of an iso-pentyl group, a neopentyl group, a tert-pentyl group, a cyclopentyl group, a methylcyclopentyl group, a dimethylcyclopentyl group, a trimethylcyclopentyl group, a tetramethylcyclopentyl group, an n-hexyl group, a 2-ethylbutyl group, a 3,3-dimethylbutyl group, a cyclohexyl group, an n-cyclohexylmethyl group, an n,n-dimethylcyclohexyl group, an n,n,n-trimethylcyclohexyl group, a tert-octyl group, a 2-ethylheyxl group, an n-nonyl group, an n-decyl group, an n-dodecyl group, an n-tetradecyl group, an n-hexadecyl group, a benzyl group, a phenethyl group, an α-methylbenzyl group, an α,α-dimethylbenzyl group, a 1-naphthylmethyl group, a 2-naphthylmethyl group, a furfuryl group, a 2-methylbenzyl group, a 3-methylbenzyl group, a 4-methylbenzyl group, a 4-ethylbenzyl group, a 4-isopropylbenzyl group, a 4-tert-butylbenzyl group, a 4-n-hexylbenzyl group, a 4-nonylbenzyl group, and a 3,4-dimethylbenzyl group.

* * * * *